(12) United States Patent
Lockwood et al.

(10) Patent No.: US 7,435,861 B2
(45) Date of Patent: Oct. 14, 2008

(54) METHODS FOR SYNTHESIS OF CAROTENOIDS, INCLUDING ANALOGS, DERIVATIVES, AND SYNTHETIC AND BIOLOGICAL INTERMEDIATES

(75) Inventors: Samuel F. Lockwood, Lago Vista, TX (US); Peng Cho Tang, Moraga, CA (US); Geoff Nadolski, Kailua, HI (US); Henry L. Jackson, Honolulu, HI (US); Zhiqiang Fang, Hawthorn Woods, IL (US); Yishu Du, Shanghai (CN); Min Yang, Vernon Hills, IL (US); William Geiss, Athens, NY (US); Richard Williams, Nashville, TN (US); David Burdick, Guilderland, NY (US)

(73) Assignee: Cardax Pharmaceuticals, Inc., Aiea, HI (US)

( * ) Notice: Subject to any disclaimer, the term of this patent is extended or adjusted under 35 U.S.C. 154(b) by 0 days.

(21) Appl. No.: 11/415,375

(22) Filed: May 1, 2006

(65) Prior Publication Data

US 2006/0293545 A1    Dec. 28, 2006

Related U.S. Application Data

(60) Provisional application No. 60/712,350, filed on Aug. 30, 2005, provisional application No. 60/702,380, filed on Jul. 26, 2005, provisional application No. 60/699,653, filed on Jul. 15, 2005, provisional application No. 60/692,682, filed on Jun. 21, 2005, provisional application No. 60/691,518, filed on Jun. 17, 2005, provisional application No. 60/675,957, filed on Apr. 29, 2005.

(51) Int. Cl.
   *C07C 403/00* (2006.01)
(52) U.S. Cl. ...................................... 585/351; 585/351
(58) Field of Classification Search ................... 585/351
   See application file for complete search history.

(56) References Cited

U.S. PATENT DOCUMENTS

2005/0009758 A1 *    1/2005    Lockwood et al. ............ 514/25

* cited by examiner

*Primary Examiner*—Yvonne Eyler
*Assistant Examiner*—Sudhakar Katakam
(74) *Attorney, Agent, or Firm*—Meyertons, Hood, Kivlin, Kowert & Goetzel, P.C.; Eric B. Meyertons

(57) ABSTRACT

A method for synthesizing intermediates for use in the synthesis of carotenoid synthetic intermediates, carotenoid analogs, and/or carotenoid derivatives. The carotenoid analog, derivative, or intermediate may be administered to a subject for the inhibition and/or amelioration of any disease that involves production of reactive oxygen species, reactive nitrogen species, radicals and/or non-radicals. In some embodiments, the invention may include methods for synthesizing chemical compounds including an analog or derivative of a carotenoid. Carotenoid analogs or derivatives may include acyclic end groups. In some embodiments, a carotenoid analog or derivative may include at least one substituent. The substituent may enhance the solubility of the carotenoid analog or derivative such that the carotenoid analog or derivative at least partially dissolves in water.

14 Claims, 1 Drawing Sheet

METHODS FOR SYNTHESIS OF CAROTENOIDS, INCLUDING ANALOGS, DERIVATIVES, AND SYNTHETIC AND BIOLOGICAL INTERMEDIATES

PRIORITY CLAIM

This application claims priority to Provisional Patent Application No. 60/675,957 entitled "METHODS FOR SYNTHESIS OF CAROTENOIDS, INCLUDING ANALOGS, DERIVATIVES, AND SYNTHETIC AND BIOLOGICAL INTERMEDIATES" filed on Apr. 29, 2005; Provisional Patent Application No. 60/691,518 entitled "METHODS FOR SYNTHESIS OF CAROTENOIDS, INCLUDING ANALOGS, DERIVATIVES, AND SYNTHETIC AND BIOLOGICAL INTERMEDIATES" filed on Jun. 17, 2005; Provisional Patent Application No. 60/692,682 entitled "METHODS FOR SYNTHESIS OF CHIRAL INTERMEDIATES OF CAROTENOIDS, CAROTENOID ANALOGS, AND CAROTENOID DERIVATIVES" filed on Jun. 21, 2005; Provisional Patent Application No. 60/699,653 entitled "METHODS FOR SYNTHESIS OF CHIRAL INTERMEDIATES OF CAROTENOIDS, CAROTENOID ANALOGS, AND CAROTENOID DERIVATIVES" filed on Jul. 15, 2005; Provisional Patent Application No. 60/702,380 entitled "METHODS FOR SYNTHESIS OF CHIRAL INTERMEDIATES OF CAROTENOIDS, CAROTENOID ANALOGS, AND CAROTENOID DERIVATIVES" filed on Jul. 26, 2005; and Provisional Patent Application No. 60/712,350 entitled "METHODS FOR SYNTHESIS OF CHIRAL INTERMEDIATES OF CAROTENOIDS, CAROTENOID ANALOGS, AND CAROTENOID DERIVATIVES" filed on Aug. 30, 2005; each of which are incorporated by reference herein.

BACKGROUND OF THE INVENTION

1. Field of the Invention

The invention generally relates to the fields of medicinal and synthetic chemistry. More specifically, the invention relates to the synthesis and use of carotenoids, including analogs, derivatives, and intermediates.

2. Description of the Relevant Art

Carotenoids are a group of natural pigments produced principally by plants, yeast, and microalgae. The family of related compounds now numbers greater than 700 described members, exclusive of Z and E isomers. At least fifty (50) carotentoids have been found in human sera or tissues. Humans and other animals cannot synthesize carotenoids de novo and must obtain them from their diet. All carotenoids share common chemical features, such as a polyisoprenoid structure, a long polyene chain forming the chromophore, and near symmetry around the central double bond. Tail-to-tail linkage of two $C_{20}$ geranylgeranyl diphosphate molecules produces the parent $C_{40}$ carbon skeleton. Carotenoids without oxygenated functional groups are called "carotenes", reflecting their hydrocarbon nature; oxygenated carotenes are known as "xanthophylls." Cyclization at one or both ends of the molecule yields 7 identified end groups (illustrative structures shown in FIG. 1).

Documented carotenoid functions in nature include light-harvesting, photoprotection, and protective and sex-related coloration in microscopic organisms, mammals, and birds, respectively. A relatively recent observation has been the protective role of carotenoids against age-related diseases in humans as part of a complex antioxidant network within cells. This role is dictated by the close relationship between the physicochemical properties of individual carotenoids and their in vivo functions in organisms. The long system of alternating double and single bonds in the central part of the molecule (delocalizing the π-orbital electrons over the entire length of the polyene chain) confers the distinctive molecular shape, chemical reactivity, and light-absorbing properties of carotenoids. Additionally, isomerism around C=C double bonds yields distinctly different molecular structures that may be isolated as separate compounds (known as Z ("cis") and E ("trans"), or geometric, isomers). Of the more than 700 described carotenoids, an even greater number of the theoretically possible mono-Z and poly-Z isomers are sometimes encountered in nature. The presence of a Z double bond creates greater steric hindrance between nearby hydrogen atoms and/or methyl groups, so that Z isomers are generally less stable thermodynamically, and more chemically reactive, than the corresponding all-E form. The all-E configuration is an extended, linear, and rigid molecule. Z-isomers are, by contrast, not simple, linear molecules (the so-called "bent-chain" isomers). The presence of any Z in the polyene chain creates a bent-chain molecule. The tendency of Z-isomers to crystallize or aggregate is much less than all-E, and Z isomers may sometimes be more readily solubilized, absorbed, and transported in vivo than their all-E counterparts. This has important implications for enteral (e.g., oral) and parenteral (e.g., intravenous, intra-arterial, intramuscular, intraperitoneal, intracoronary, and subcutaneous) dosing in mammals.

Carotenoids, (e.g., astaxanthin), are potent direct radical scavengers and singlet oxygen quenchers and possess all the desirable qualities of such therapeutic agents for inhibition or amelioration of ischemia-reperfusion injury. Synthesis of novel carotenoid derivatives with "soft-drug" properties (i.e. active as antioxidants in the derivatized form), with physiologically relevant, cleavable linkages to pro-moieties, can generate significant levels of free carotenoids in both plasma and solid organs. In the case of non-esterified, free astaxanthin, this is a particularly useful embodiment (characteristics specific to non-esterified, free astaxanthin below):

- Lipid soluble in natural form; may be modified to become more water soluble;
- Molecular weight of 597 Daltons (size <600 daltons (Da) readily crosses the blood brain barrier, or BBB);
- Long polyene chain characteristic of carotenoids effective in singlet oxygen quenching and lipid peroxidation chain breaking; and
- No pro-vitamin A activity in mammals (eliminating concerns of hypervitaminosis A and retinoid toxicity in humans).

The administration of antioxidants which are potent singlet oxygen quenchers and direct radical scavengers, particularly of superoxide anion, should limit hepatic fibrosis and the progression to cirrhosis by affecting the activation of hepatic stellate cells early in the fibrogenetic pathway. Reduction in the level of "Reactive Oxygen Species" (ROS) by the administration of a potent antioxidant can therefore be crucial in the prevention of the activation of both "hepatic stellate cells" (HSC) and Kupffer cells. This protective antioxidant effect appears to be spread across the range of potential therapeutic antioxidants, including water-soluble (e.g., vitamin C, glutathione, resveratrol) and lipophilic (e.g., vitamin E, β-carotene, astaxanthin) agents. Therefore, a co-antioxidant derivative strategy in which water-soluble and lipophilic agents are combined synthetically is a particularly useful embodiment. Examples of uses of carotenoid derivatives and analogs are illustrated in U.S. patent application Ser. No. 10/793,671 filed on Mar. 4, 2004, entitled "CAROTENOID ETHER ANALOGS OR DERIVATIVES FOR THE INHIBITION AND AMELIORATION OF DISEASE" to Lockwood et al. published on Jan. 13, 2005, as Publication No. US-2005-0009758 and PCT International Application Number PCT/US2003/023706 filed on Jul. 29, 2003, entitled "STRUCTURAL CAROTENOID ANALOGS FOR THE INHIBITION AND AMELIORATION OF DISEASE" to Lockwood et al. (International Publication Number WO 2004/011423 A2, published on Feb. 5, 2004) both of which are incorporated by reference as if fully set forth herein.

Problems related to the use of some carotenoids and structural carotenoid analogs or derivatives include: (1) the complex isomeric mixtures, including non-carotenoid contaminants, provided in natural and synthetic sources leading to costly increases in safety and efficacy tests required by such agencies as the FDA; (2) limited bioavailability upon administration to a subject; and (3) the differential induction of cytochrome P450 enzymes (this family of enzymes exhibits species-specific differences which must be taken into account when extrapolating animal work to human studies). Selection of the appropriate analog or derivative and isomer composition for a particular application increases the utility of carotenoid analogs or derivatives for the uses defined herein.

Synthesis of an appropriate analog or derivative and isomer composition requires a supply of starting materials (e.g., carotenoids, carotenoid synthetic intermediates). Any new synthetic route which is more efficient to a carotenoid analog or derivative and/or synthetic intermediate would be beneficial. More efficient synthetic routes would provide a more stable source of starting materials (e.g., carotenoids) which may be difficult or expensive to extract from natural sources. Synthetic routes to natural products may facilitate the synthesis of analogs and derivatives of the natural products.

SUMMARY

In some embodiments, a chemical composition may include one or more carotenoid analogs or derivatives having a general structure:

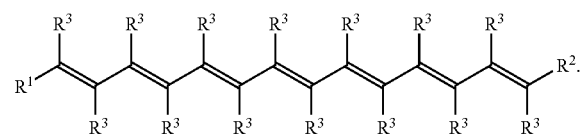

Each $R^3$ may be independently hydrogen or methyl. Each $R^1$ and $R^2$ may be independently:

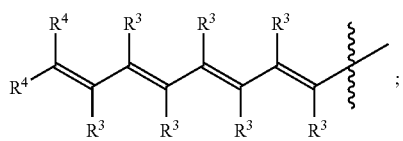

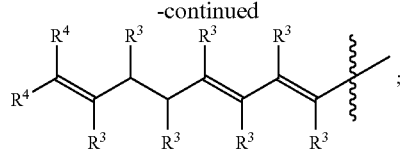

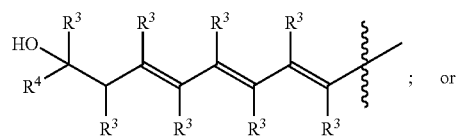

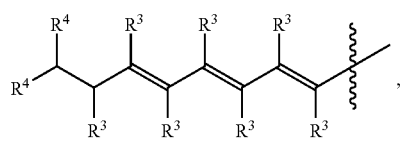

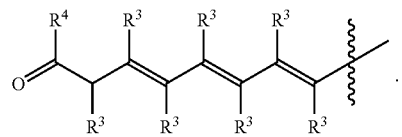

Each $R^4$ may be independently hydrogen, —OH, =O, —CH$_2$OH, or —OR$^5$. At least one $R^4$ group is —OR$^5$; wherein each $R^5$ is independently: alkyl; aryl; -alkyl-N(R$^7$)$_2$; -aryl-N(R$^7$)$_2$; -alkyl-N$^+$(R$^7$)$_3$; -aryl-N$^+$(R$^7$)$_3$; -alkyl-CO$_2$R$^7$; -aryl-CO$_2$R$^7$; -alkyl-CO$_2^-$; -aryl-CO$_2^-$; —CO$_2$R$^8$; —P(O)(OR$^8$)$_2$; —S(O)(OR$^8$)$_2$; an amino acid; a peptide, a carbohydrate; —C(O)—(CH$_2$)$_n$—CO$_2$R$^9$; a nucleoside residue, or a co-antioxidant. $R^7$ may be hydrogen, alkyl, or aryl. $R^8$ may be hydrogen, alkyl, aryl, benzyl or a co-antioxidant. $R^9$ may be hydrogen; alkyl; aryl; —P(O)(OR$^8$)$_2$; —S(O)(OR$^8$)$_2$; an amino acid; a peptide, a carbohydrate; a nucleoside, or a co-antioxidant. n may be 1 to 9.

In some embodiments, each $R^4$ may be independently hydrogen, —OH, —CH$_2$OH, or —OR$^5$. At least one $R^4$ group may be —OR$^5$. Each $R^5$ may be independently: alkyl; aryl; —P(O)(OR$^8$)$_2$; an amino acid; a peptide, a carbohydrate; —C(O)—(CH$_2$)$_n$—CO$_2$R$^9$; a nucleoside residue, or a co-antioxidant. $R^8$ may be hydrogen, alkyl, aryl, benzyl or a co-antioxidant. $R^9$ may be hydrogen; alkyl; aryl; —P(O)(OR$^8$)$_2$; an amino acid; a peptide, a carbohydrate; a nucleoside, or a co-antioxidant. n may be 1 to 9.

In some embodiments, a chemical composition may include one or more carotenoid derivatives or analogs having the structure:

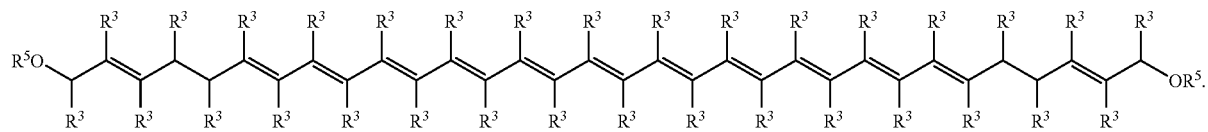

Each $R^3$ may be independently hydrogen or methyl. At least one $R^4$ group is —$OR^5$. Each $R^5$ may be independently: alkyl; aryl; —$P(O)(OR^8)_2$; —$C(O)$—$(CH_2)_n$—$CO_2R^9$; or a co-antioxidant. $R^8$ may be hydrogen, alkyl, aryl, benzyl or a co-antioxidant. $R^9$ may be hydrogen; alkyl; aryl; —$P(O)(OR^8)_2$; or a co-antioxidant. n may be 1 to 9.

In some embodiments, a chemical composition may include one or more carotenoid derivatives or analogs having the structure:

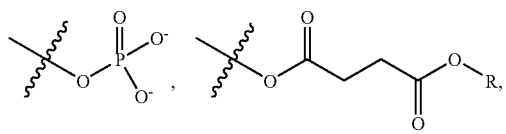

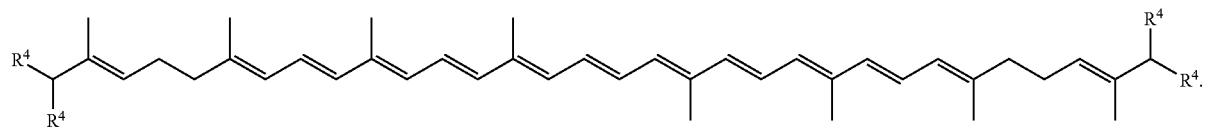

Each $R^4$ may be independently hydrogen, —OH, —$CH_2OH$, or —$OR^5$. Each $R^5$ may be independently: alkyl; aryl; —$P(O)(OR^8)_2$; —$C(O)$—$(CH_2)_n$—$CO_2R^9$; or a co-antioxidant. $R^8$ may be hydrogen, alkyl, aryl, benzyl or a co-antioxidant. $R^9$ may be hydrogen; alkyl; aryl; —$P(O)(OR^8)_2$; or a co-antioxidant. n may be 1 to 9.

-continued

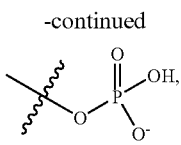

In some embodiments, a chemical composition may include one or more carotenoid derivatives or analogs having the structure:

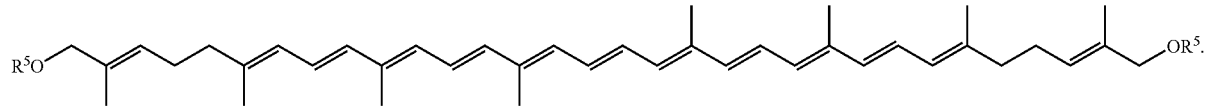

Each —$OR^5$ may be independently:

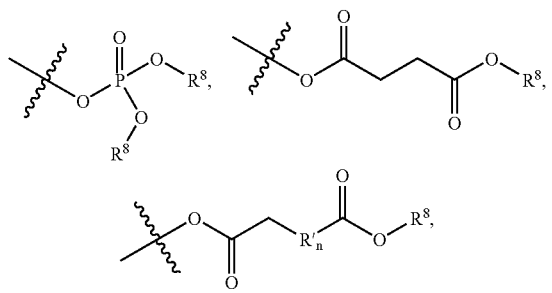

-continued

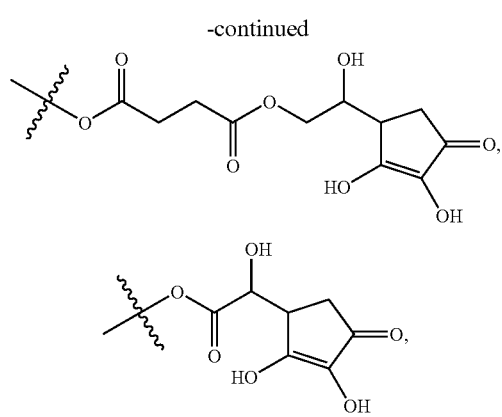

or a co-antioxidant. $R^8$ may be hydrogen, alkyl, aryl, benzyl, Group IA metal, or a co-antioxidant. R' may be $CH_2$. n may be 1 to 9.

In some embodiments, each —$OR^5$ may independently include:

-continued

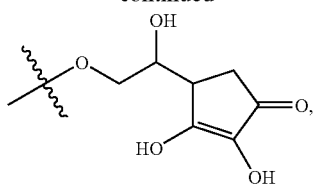

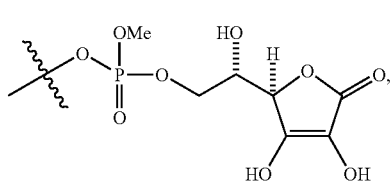

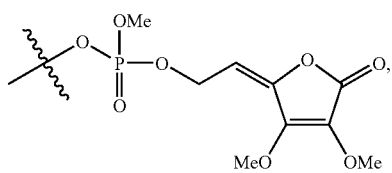

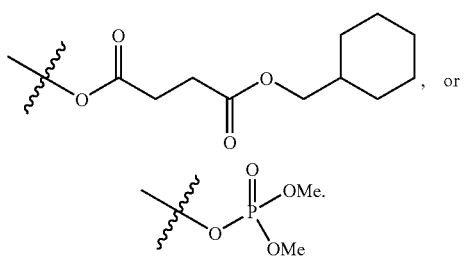

Each R may be independently H, alkyl, aryl, benzyl, Group IA metal, or co-antioxidant.

In some embodiments, each —$OR^5$ may independently include:

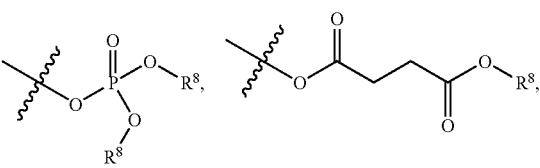

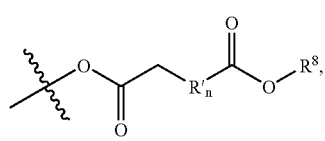

or a co-antioxidant. $R^8$ may be hydrogen, alkyl, aryl, benzyl, Group IA metal, or a co-antioxidant. R' may be $CH_2$. n may be 1 to 9.

In some embodiments, a composition may include one or more carotenoid derivatives or analogs having the structures:

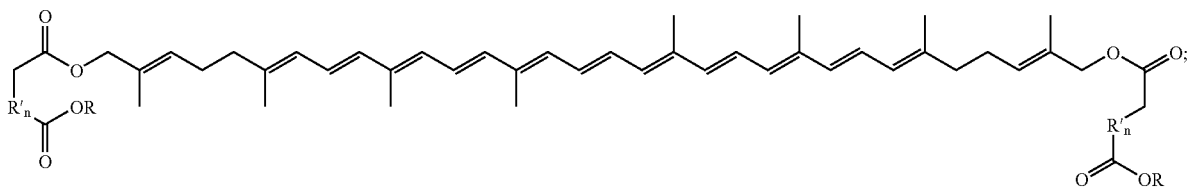

wherein each R is independently H, alkyl, aryl, benzyl, Group IA metal, or a co-antioxidant.

In some embodiments, a composition may include one or more carotenoid derivatives or analogs having the structures:

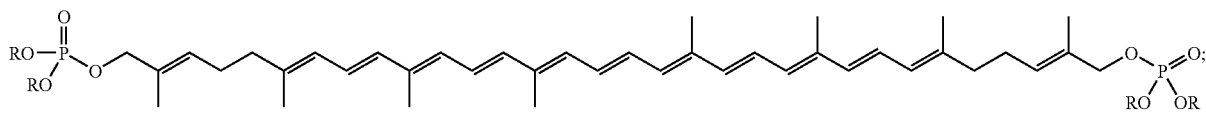

wherein each R is independently H, alkyl, aryl, benzyl, Group IA metal, or a co-antioxidant.

In some embodiments, a composition may include one or more carotenoid derivatives or analogs having the structures:

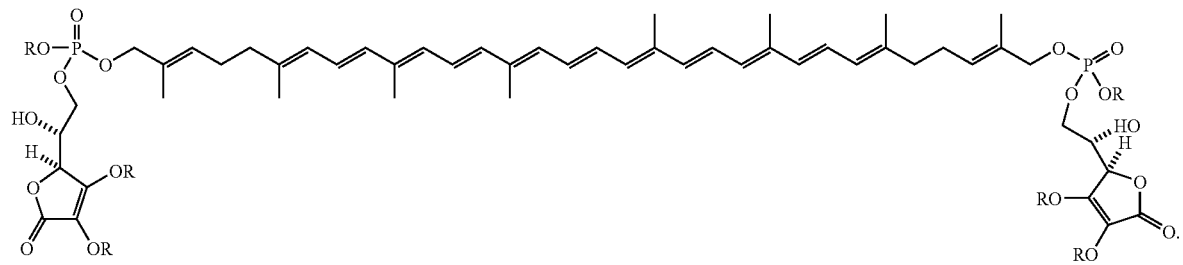

Each R may be independently H, alkyl, aryl, benzyl, or a Group IA metal.

In some embodiments, a carotenoid analog or derivative is an analog or derivative of a naturally occurring carotenoid.

In some embodiments, substituent $R^5$ in at least a portion of the carotenoid analogs or derivatives administered to the subject may be cleaved during use. The cleavage product may be biologically active. Cleavage of a carotenoid analog or derivative is carried out by one or more enzymes.

In some embodiments, a distance between $R^1$ and $R^2$ is between about 25 Å to about 55 Å. The distance between $R^1$ and $R^2$ is between about 40 Å to about 45 Å.

In some embodiments, a co-antioxidant may include Vitamin C, Vitamin C analogs, Vitamin C derivatives, Vitamin E, Vitamin E analogs, Vitamin E derivatives, flavonoids, flavonoid derivatives, or flavonoid analogs.

In some embodiments, flavonoids may include quercetin, xanthohumol, isoxanthohumol, or genistein.

In some embodiments, a composition may include a carotenoid analog or derivative that at least partially dissolves in water.

In some embodiments, one or more carotenoid derivatives or analogs may be synthetically derived.

A synthetic route to a carotenoid, carotenoid analog or derivative and/or synthetic intermediate is presented. In some embodiments, methods and reactions described herein may be used to synthesize naturally-occurring carotenoids. Naturally-occurring carotenoids may include astaxanthin as well as other carotenoids including, but not limited to, zeaxanthin, carotenediol, nostoxanthin, crustaxanthin, canthaxanthin, isozeaxanthin, hydroxycanthaxanthin, tetrahydroxy-carotene-dione, lutein, lycophyll, and lycopene.

In some embodiments, a method of synthesizing a compound may include using a synthesized compound as a chemical intermediate in the synthesis of a carotenoid, a carotenoid intermediate, a carotenoid analog, and/or a carotenoid derivative. The synthesized compound may include substituents to increase the solubility (e.g., water) of the final synthetic product.

In certain embodiments, carotenoids, carotenoid derivatives, or carotenoid analogs which may be synthesized from the chemical intermediate having the general structure

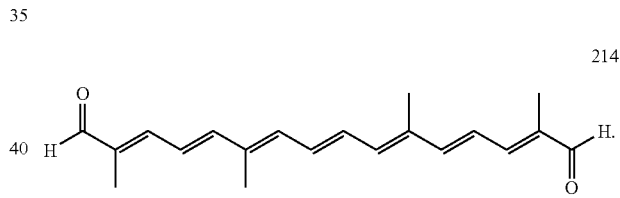

214

Compound 214 may be coupled to a phosphonium salt product 216 having the general structure

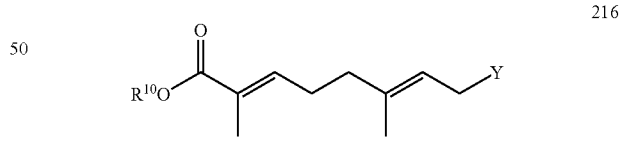

216 to form protected carotenoid 218 having the general structure

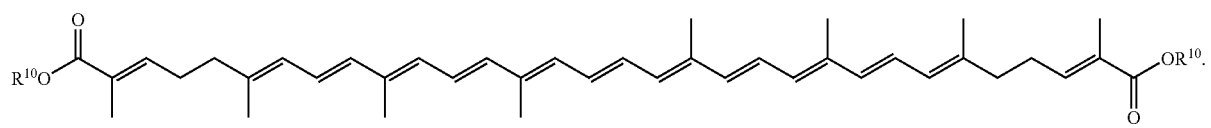

218

In some embodiments, Y may be $PR^{11}_3$ or $P(=O)(OR^{11})_2$. $R^{10}$ may be $SiR^5_3$, H, alkyl, or aryl. $R^{11}$ may be alkyl or aryl.

In some of the phosphonium salt product 216 embodiments, Y may be $PR^{11}_3$, $R^{11}$ may be phenyl, and such that phosphonium salt product 216 has the general structure

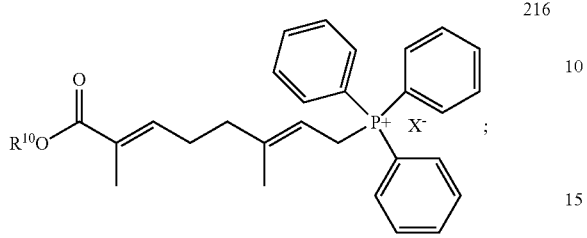

216

In some embodiments, X may be F, Cl, Br, or I.

In some embodiments, a method may include reducing protected carotenoid 218 to form carotenoid 220 having the general structure

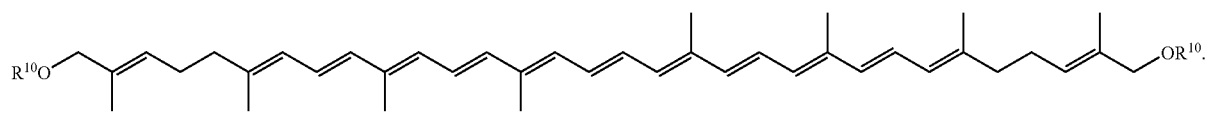

220

In some embodiments, $R^{10}$ may be $SiR^{11}_3$, H, alkyl, or aryl.

In some embodiments, a method may include condensing reduced carotenoid 220 with succinic anhydride to form compound 222 having the general structure

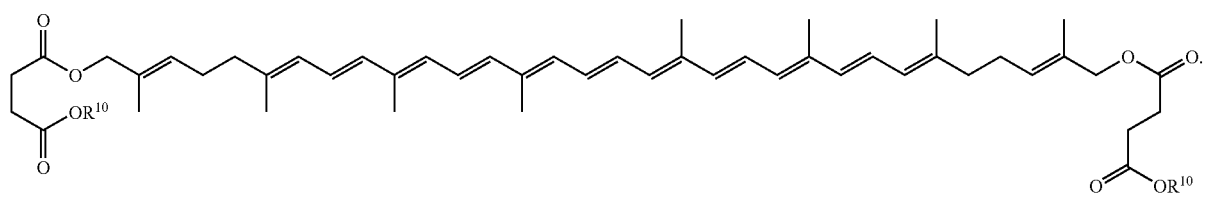

222

In some embodiments, $R^{10}$ may be $SiR^{11}_3$, H, alkyl, or aryl. The method of may include forming a salt 224 of compound 226 having a general structure

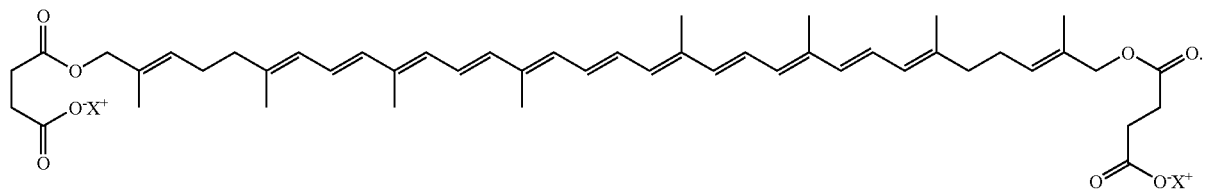

224 some embodiments, X may be a counterion. X may form inorganic salts and/or organic salts.

In some embodiments, a method may include phosphorylating carotenoid 220 to form compound 226 having the general structure

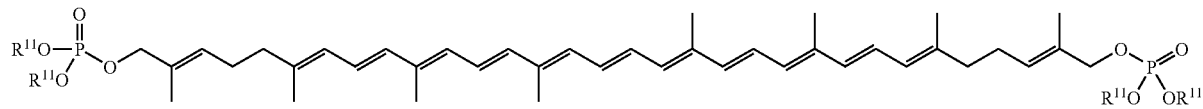

221. $R^{11}$ may be alkyl, benzyl, or aryl. The method may include forming a salt 223 of compound 226 having a general structure

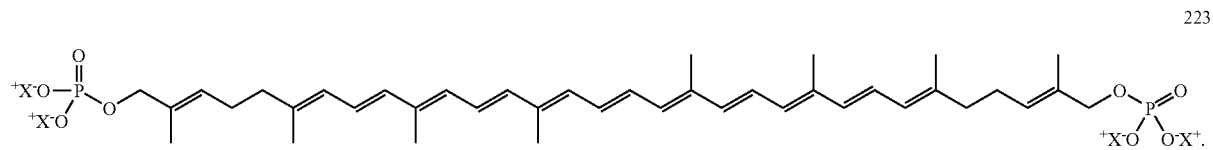

In some embodiments, X may be a counterion. X may include inorganic salts and/or organic salts.

In some embodiment, a method may include preparing phosphonium salt product 216 by oxidizing ester 228 having the general structure

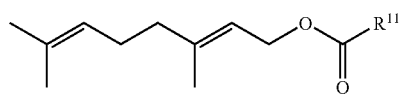

to form aldehyde 230 having the general structure

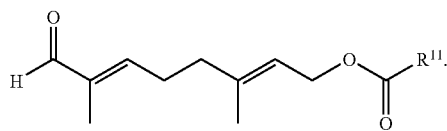

The method may include oxidizing aldehyde 230 to form oxidized product 232 having the general structure

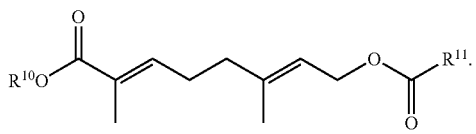

Oxidized product 232 may be selectively reduced or deprotected to form reduced product 234 having the general structure

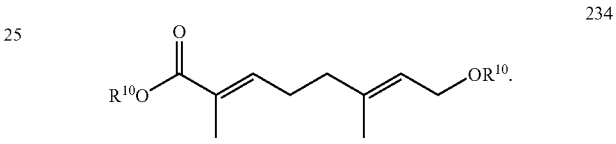

Conversion of product 232 to product 234 may be viewed as more of a deprotection of an alcohol. The method may include halogenating reduced product 234 to form halogenated product 236 having the general structure

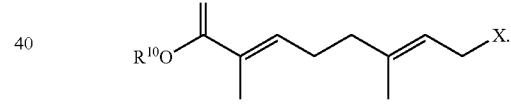

Halogenated product 236 may be converted to the phosphonium salt product 216. In some embodiments, X may be a counterion. X may include inorganic salts and/or organic salts. X may include F, Cl, Br, or I. $R^{10}$ may be $SiR^{11}{}_3$, H, alkyl, or aryl. $R^{11}$ may be alkyl, benzyl, or aryl.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings.

Figure 1:
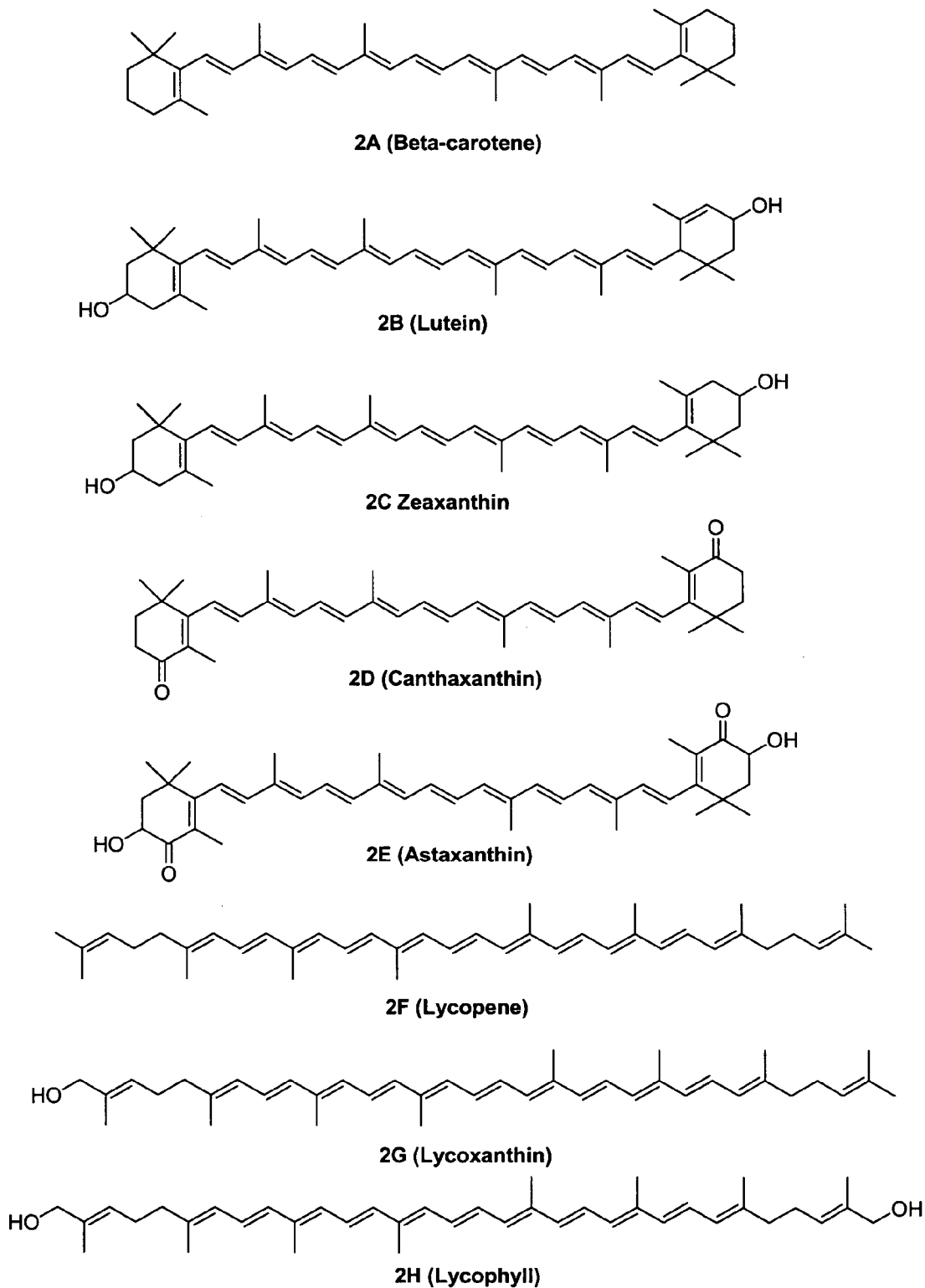
FIG. 1 depicts a graphic representation of several examples of the structures of several carotenoids that may be used according to some embodiments.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

Compounds described herein embrace both racemic and optically active compounds. Chemical structures depicted herein that do not designate specific stereochemistry are intended to embrace all possible stereochemistries.

Compounds described herein embrace isomer mixtures, racemic, optically active, and optically inactive stereoisomers and compounds.

It will be appreciated by those skilled in the art that compounds having one or more chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound. As used herein, the term "single stereoisomer" refers to a compound having one or more chiral centers that, while it can exist as two or more stereoisomers, are isolated in greater than about 95% excess of one of the possible stereoisomers. As used herein a compound that has one or more chiral centers is considered to be "optically active" when isolated or used as a single stereoisomer.

Definitions

Unless defined otherwise, all technical and scientific terms used herein have the same meaning as commonly understood by one of ordinary skill in the art.

The term "acyl," as used herein, generally refers to a carbonyl substituent, —C(O)R, where R is alkyl or substituted alkyl, aryl, or substituted aryl, which may be called an alkanoyl substituent when R is alkyl.

The terms "administration," "administering," or the like, as used herein, when used in the context of providing a pharmaceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered by parenteral, subcutaneous, intravenous, intracoronary, rectal, intramuscular, intraperitoneal, transdermal, or buccal routes of delivery. Alternatively, or concurrently, administration may be by the oral route. The dosage administered will be dependent upon the age, health, weight, and/or disease state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

The terms "alkenyl" and "olefin," as used herein, generally refer to any structure or moiety having the unsaturation C=C. As used herein, the term "alkynyl" generally refers to any structure or moiety having the unsaturation C≡C.

The term "alkoxy," as used herein, generally refers to an —OR group, where R is an alkyl, substituted lower alkyl, aryl, substituted aryl. Alkoxy groups include, for example, methoxy, ethoxy, phenoxy, substituted phenoxy, benzyloxy, phenethyloxy, t-butoxy, and others.

The term "alkyl," as used herein, generally refers to a chemical substituent containing the monovalent group $C_nH_{2n}$, where n is an integer greater than zero. Alkyl includes a branched or unbranched monovalent hydrocarbon radical. An "n-mC" alkyl or "(nC-mC)alkyl" refers to all alkyl groups containing from n to m carbon atoms. For example, a 1-4C alkyl refers to a methyl, ethyl, propyl, or butyl group. All possible isomers of an indicated alkyl are also included. Thus, propyl includes isopropyl, butyl includes n-butyl, isobutyl and t-butyl, and so on. The term alkyl includes substituted alkyls. For example, alkyl includes, but is not limited to: methyl, ethyl, propyl, isopropyl, butyl, iso-butyl, sec-butyl, pentyl, 3-pentyl, hexyl, heptyl, octyl, nonyl, decyl, undecyl, dodecyl, tridecyl, tetradecyl or pentadecyl; "alkenyl" includes but is not limited to vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl, 13-tetradeceny, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, 14-pentadecenyl; "alkoxy" includes but is not limited to methoxy, ethoxy, propoxy, isopropoxy, butoxy, iso-butoxy, sec-butoxy, pentoxy, 3-pentoxy, hexoxy, heptyloxy, octyloxy, nonyloxy, decyloxy, undecyloxy, dodecyloxy, tridecyloxy, tetradecyloxy, or pentadecyloxy.

The term "amino," as used herein, generally refers to a group —NRR', where R and R' may independently be hydrogen, lower alkyl, substituted lower alkyl, aryl, substituted aryl or acyl.

The terms "amphiphile" or "amphiphilic," as used herein, refer to a molecule or species, which exhibits both hydrophilic and lipophilic character. In general, an amphiphile contains a lipophilic moiety and a hydrophilic moiety. The terms "lipophilic" and "hydrophobic" are interchangeable as used herein. An amphiphile may form a Langmuir film. An amphiphile may be surface-active in solution. A bolaamphiphile is a special case in which the hydrophobic spacer is substituted on each end with a hydrophilic moiety.

Non-limiting examples of hydrophobic groups or moieties include lower alkyl groups, alkyl groups having 7, 8, 9, 10, 11, 12, or more carbon atoms, including alkyl groups with 14-30, or 30 or more carbon atoms, substituted alkyl groups, alkenyl groups, alkynyl groups, aryl groups, substituted aryl groups, saturated or unsaturated cyclic hydrocarbons, heteroaryl, heteroarylalkyl, heterocyclic, and corresponding substituted groups. A hydrophobic group may contain some hydrophilic groups or substituents insofar as the hydrophobic character of the group is not outweighed. In further variations, a hydrophobic group may include substituted silicon atoms, and may include fluorine atoms. The hydrophobic moieties may be linear, branched, or cyclic.

Non-limiting examples of hydrophilic groups or moieties include hydroxyl, methoxy, phenyl, carboxylic acids and salts thereof, methyl, ethyl, and vinyl esters of carboxylic acids, amides, amino, cyano, isocyano, nitrile, ammonium salts, sulfonium salts, phosphonium salts, mono- and di-alkyl substituted amino groups, polypropyleneglycols, polyethylene glycols, epoxy groups, acrylates, sulfonamides, nitro, $-OP(O)(OCH_2CH_2N^+RRR)O^-$, guanidinium, aminate, acrylamide, pyridinium, piperidine, and combinations thereof, wherein each R is independently selected from H or alkyl. Further examples include polymethylene chains substituted with alcohol, carboxylate, acrylate, or methacrylate. Hydrophilic moieties may also include alkyl chains having internal amino or substituted amino groups, for example, internal $-NH-$, $-NC(O)R-$, or $-NC(O)CH=CH_2-$ groups, wherein R is H or alkyl. Hydrophilic moieties may also include polycaprolactones, polycaprolactone diols, poly(acetic acid)s, poly(vinyl acetates)s, poly(2-vinyl pyridine)s, cellulose esters, cellulose hydroxylethers, poly(L-lysine hydrobromide)s, poly(itaconic acid)s, poly(maleic acid)s, poly(styrenesulfonic acid)s, poly(aniline)s, or poly(vinyl phosphonic acid)s. A hydrophilic group may contain some hydrophobic groups or substituents insofar as the hydrophilic character of the group is not outweighed.

The term "analog," as used herein, generally refers to a compound that resembles another in structure but is not necessarily an isomer.

The term "antioxidant," as used herein, generally refers to any of various substances (e.g., beta-carotene, vitamin C, vitamin E, flavonoids, polyphenolics, and alpha-tocopherol) that inhibit oxidation or reactions promoted by oxygen and peroxides and that include many held to protect the living body from the deleterious effects of free radicals.

The term "arrhythmia," as used herein, generally refers to any variation from the normal rhythm of the heart beat, including sinus arrhythmia, premature beat, heart block, atrial fibrillation, atrial flutter, ventricular tachycardia, ventricular fibrillation, torsades de pointes, pulsus alternans and paroxysmal tachycardia.

The term "aryl," as used herein, generally refers to a chemical substituent containing an aromatic group. An aromatic group may be a single aromatic ring or multiple aromatic rings that are fused together, coupled covalently, or coupled to a common group such as a methylene, ethylene, or carbonyl, and includes polynuclear ring structures. An aromatic ring or rings may include, but is not limited to, substituted or unsubstituted phenyl, naphthyl, biphenyl, diphenylmethyl, and benzophenone groups. The term "aryl" includes substituted aryls.

The term "cardiac arrhythmia," as used herein, generally refers to a disturbance of the electrical activity of the heart that manifests as an abnormality in heart rate or heart rhythm. Arrhythmia is most commonly related to cardiovascular disease, and in particular, ischemic heart disease.

The term "cancer," as used herein, generally refers to the uncontrolled, abnormal growth of cells. In particular, cancer may refer to tissue in a diseased state including pre-cancerous, carcinogen-initiated and carcinogen-transformed cells.

The terms such as "carotenoid analog" and "carotenoid derivative," as used herein, generally refer to chemical compounds or compositions derived from a naturally occurring or synthetic carotenoid. Terms such as carotenoid analog and carotenoid derivative may also generally refer to chemical compounds or compositions that are synthetically derived from non-carotenoid based parent compounds; however, which ultimately substantially resemble a carotenoid derived analog. Non-limiting examples of carotenoid analogs and derivatives that may be used according to some of the embodiments described herein are depicted schematically in FIG. 1, D-G. "Derivative" in the context of this application is generally defined as a chemical substance derived from another substance either directly or by modification or partial substitution. "Analog" in the context of this application is generally defined as a compound that resembles another in structure but is not necessarily an isomer. Typical analogs or derivatives include molecules which demonstrate equivalent or improved biologically useful and relevant function, but which differ structurally from the parent compounds. Parent carotenoids are selected from the more than 700 naturally occurring carotenoids described in the literature, and their stereo- and geometric isomers. Such analogs or derivatives may include, but are not limited to, esters, ethers, carbonates, amides, carbamates, phosphate esters and ethers, sulfates, glycoside ethers, with or without spacers (linkers).

The term "co-antioxidant," as used herein, generally refers to an antioxidant that is used and that acts in combination with another antioxidant (e.g., two antioxidants that are chemically and/or functionally coupled, or two antioxidants that are combined and function with each another in a pharmaceutical preparation). The effects of co-antioxidants may be additive (i.e., the anti-oxidative potential of one or more anti-oxidants acting additively is approximately the sum of the oxidative potential of each component anti-oxidant) or synergistic (i.e., the anti-oxidative potential of one or more anti-oxidants acting synergistically may be greater than the sum of the oxidative potential of each component anti-oxidant).

The term "counterion," as used herein, generally refers to a second ion of opposite charge that is also necessarily present with a first ion.

The terms "coupling" and "coupled," as used herein, with respect to molecular moieties or species, atoms, synthons, cyclic compounds, and nanoparticles refers to their attachment or association with other molecular moieties or species, atoms, synthons, cyclic compounds, and nanoparticles. The attachment or association may be specific or non-specific, reversible or non-reversible, the result of chemical reaction, or complexation or charge transfer. The bonds formed by a coupling reaction are often covalent bonds, or polar-covalent bonds, or mixed ionic-covalent bonds, and may sometimes be Coulombic forces, ionic or electrostatic forces or interactions.

The term "cycloalkyl," as used herein, includes, but is not limited to, cyclopropyl, cyclobutyl, cyclopentyl, cyclohexyl, cycloheptyl, or cyclooctyl.

The term "derivative," as used herein, generally refers to a chemical substance derived from another substance either directly or by modification or partial substitution.

The term "functionalized," as used herein, generally refers to the presence of a reactive chemical moiety or functionality. A functional group may include, but is not limited to, chemical groups, biochemical groups, organic groups, inorganic groups, organometallic groups, aryl groups, heteroaryl groups, cyclic hydrocarbon groups, amino (—NH$_2$), hydroxyl (—OH), cyano (—C≡N), nitro (NO$_2$), carboxyl (—COOH), formyl (—CHO), keto (—CH$_2$C(O)CH$_2$—), ether (—CH$_2$—O—CH$_2$—), thioether (—CH$_2$—S—CH$_2$—), alkenyl (—C=C—), alkynyl, (—C≡C—), epoxy (e.g.,

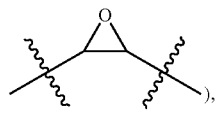

), metalloids (functionality containing Si and/or B) and halo (F, Cl, Br, and I) groups. In some embodiments, the functional group is an organic group.

The term "heteroaryl," as used herein, generally refers to a completely unsaturated heterocycle.

The term "heterocycle," as used herein, generally refers to a closed-ring structure, in which one or more of the atoms in the ring is an element other than carbon. Heterocycle may include aromatic compounds or non-aromatic compounds. Heterocycles may include rings such as thiophene, pyridine, isoxazole, phthalimide, pyrazole, indole, furan, or benzo-fused analogs of these rings. Examples of heterocycles include tetrahydrofuran, morpholine, piperidine, pyrrolidine, and others. In some embodiments, "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms (e.g., N, O, and S) and wherein the nitrogen and sulfur heteroatoms may optionally be oxidized, and the nitrogen may optionally be quaternized, and including any bicyclic group in which any of the above-defined heterocyclic rings is fused to a benzene ring. In some embodiments, heterocycles may include cyclic rings including boron atoms. The heterocyclic ring may be attached to its pendant group at any heteroatom or carbon atom that results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles.

The term "ischemia-reperfusion injury," as used herein, generally refers to the pathology attributed to reoxygenation of previously ischemic tissue (either chronically or acutely ischemic), which includes atherosclerotic and thromboembolic vascular disease and its related illnesses. Major diseases or processes including myocardial infarction, stroke, peripheral vascular disease, venous or arterial occlusion and/or restenosis, organ transplantation, coronary artery bypass graft surgery, percutaneous transluminal coronary angioplasty, and cardiovascular arrest and/or death are included, but are not seen as limiting for other pathological processes which involve reperfusion of ischemic tissue in their individual pathologies.

The terms "in need of treatment" or "in need thereof," as used herein, when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

The term "ion," as used herein, generally refers to an atom(s), radical, or molecule(s) that has lost or gained one or more electrons and has thus acquired an electric charge.

The term "nutraceuticals," as used herein, generally refers to dietary supplements, foods, or medical foods that: 1. possess health benefits generally defined as reducing the risk of a disease or health condition, including the management of a disease or health condition or the improvement of health; and 2. are safe for human consumption in such quantity, and with such frequency, as required to realize such properties.

The terms "oligomeric" and "polymeric," as used herein, are used interchangeably herein to generally refer to multimeric structures having more than one component monomer or subunit.

The term "organ," as used herein, when used in reference to a part of the body of an animal or of a human generally refers to the collection of cells, tissues, connective tissues, fluids and structures that are part of a structure in an animal or a human that is capable of performing some specialized physiological function. Groups of organs constitute one or more specialized body systems. The specialized function performed by an organ is typically essential to the life or to the overall well-being of the animal or human. Non-limiting examples of body organs include the heart, lungs, kidney, ureter, urinary bladder, adrenal glands, pituitary gland, skin, prostate, uterus, reproductive organs (e.g., genitalia and accessory organs), liver, gall-bladder, brain, spinal cord, stomach, intestine, appendix, pancreas, lymph nodes, breast, salivary glands, lacrimal glands, eyes, spleen, thymus, bone marrow. Non-limiting examples of body systems include the respiratory, circulatory, cardiovascular, lymphatic, immune, musculoskeletal, nervous, digestive, endocrine, exocrine, hepato-biliary, reproductive, and urinary systems. In animals, the organs are generally made up of several tissues, one of which usually predominates, and determines the principal function of the organ.

Terms such as "pharmaceutical composition," "pharmaceutical formulation," "pharmaceutical preparation," or the like, as used herein, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release" or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

The term "pharmaceutically acceptable salts," as used herein, includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

The terms "pharmaceutically or nutraceutically acceptable formulation," as used herein, generally refers to a non-toxic formulation containing a predetermined dosage of a pharmaceutical and/or nutraceutical composition, wherein the dosage of the pharmaceutical and/or nutraceutical composition is adequate to achieve a desired biological outcome. The meaning of the term may generally include an appropriate delivery vehicle that is suitable for properly delivering the pharmaceutical composition in order to achieve the desired biological outcome.

The term "pharmacologically inert," as used herein, generally refers to a compound, additive, binder, vehicle, and the like, that is substantially free of any pharmacologic or "drug-like" activity.

The term "polymerizable element," as used herein, generally refers to a chemical substituent or moiety capable of undergoing a self-polymerization and/or co-polymerization reaction (e.g., vinyl derivatives, butadienes, trienes, tetraenes, diolefins, acetylenes, diacetylenes, styrene derivatives).

The term "precursor of a substituent" as used herein, generally refers to a molecule comprising a labile leaving group which allows facile reaction of the substituent with an available nucleophile.

The phrase "prophylactically effective amount," as used herein, generally refers to an amount of a pharmaceutical composition that will substantially prevent, delay or reduce the risk of occurrence of the biological or physiological event in a cell, a tissue, a system, animal or human that is being sought by a researcher, veterinarian, physician or other caregiver.

The terms "$R''$," as used herein, in a chemical formula refer to hydrogen or a functional group, each independently selected, unless stated otherwise. In some embodiments the functional group may be an organic group. In some embodiments the functional group may be an alkyl group. In some embodiment, the functional group may be a hydrophobic or hydrophilic group.

The terms "reducing," "inhibiting" and "ameliorating," as used herein, when used in the context of modulating a pathological or disease state, generally refers to the prevention and/or reduction of at least a portion of the negative consequences of the disease state. When used in the context of an adverse side effect associated with the administration of a drug to a subject, the term(s) generally refer to a net reduction in the severity or seriousness of said adverse side effects.

The term "stereoselective reduction" may be generally defined as stereo chemical reduction by which one of a pair of enantiomers, each having at least one asymmetric carbon atom, is produced selectively, i.e., in an amount larger than that of the other enantiomer. The stereo-differentiating reduction is classified into enantioface- and diastereo-differentiating reductions, by which optical isomers having one asymmetric carbon atom and those having two asymmetric carbon atoms are produced, respectively.

In some embodiments, a carbonyl may be stereoselectively reduced such that the resulting chiral center comprises a stereochemistry of R or S comprising a stereoselectivity of greater than 50%. A stereoselectivity of a reduction may be greater than 75%. A stereoselectivity of a reduction may be greater than 90%. A stereoselectivity of a reduction may be greater than 95%. A stereoselectivity of a reduction may be greater than 99%.

The term "subject," as used herein, may be generally defined as all mammals, in particular humans.

The term "substituted alkyl," as used herein, generally refers to an alkyl group with an additional group or groups attached to any carbon of the alkyl group. Substituent groups may include one or more functional groups such as alkyl, lower alkyl, aryl, acyl, halogen, alkylhalo, hydroxy, amino, alkoxy, alkylamino, acylamino, acyloxy, aryloxy, aryloxyalkyl, mercapto, both saturated and unsaturated cyclic hydrocarbons, heterocycles, and other organic groups.

The term "substituted aryl," as used herein, generally refers to an aryl group with an additional group or groups attached to any carbon of the aryl group. Additional groups may include one or more functional groups such as lower alkyl, aryl, acyl, halogen, alkylhalo, hydroxy, amino, alkoxy, alkylamino, acylamino, acyloxy, aryloxy, aryloxyalkyl, thioether, heterocycles, both saturated and unsaturated cyclic hydrocarbons which are fused to the aromatic ring(s), coupled covalently or coupled to a common group such as a methylene or ethylene group, or a carbonyl coupling group such as in cyclohexyl phenyl ketone, and others.

The term "substituted heterocycle," as used herein, generally refers to a heterocyclic group with an additional group or groups attached to any element of the heterocyclic group.

Additional groups may include one or more functional groups such as lower alkyl, aryl, acyl, halogen, alkylhalos, hydroxy, amino, alkoxy, alkylamino, acylamino, acyloxy, aryloxy, aryloxyalkyl, thioether, heterocycles, both saturated and unsaturated cyclic hydrocarbons which are fused to the heterocyclic ring(s), coupled covalently or coupled to a common group such as a methylene or ethylene group, or a carbonyl coupling group such as in cyclohexyl phenyl ketone, and others.

The term "substrate," as used herein, generally refers to a body or base layer or material (e.g., onto which other layers are deposited).

The phrase "the synergistic combination of more than one structural analog or derivative or synthetic intermediate of carotenoids," as used herein, may be generally defined as any composition including one structural carotenoid analog or derivative or synthetic intermediate combined with one or more other structural carotenoid analogs or derivatives or synthetic intermediate or co-antioxidants, either as derivatives or in solutions and/or formulations, where the therapeutic property of the combination of compounds is greater than the sum of the potential therapeutic property of the individual compounds.

The phrase "therapeutically effective amount," as used herein, generally refers to an amount of a drug or pharmaceutical composition that will elicit at least one desired biological or physiological response of a cell, a tissue, a system, animal or human that is being sought by a researcher, veterinarian, physician or other caregiver.

The term "thioether," as used herein, generally refers to the general structure R—S—R' in which R and R' are the same or different and may be alkyl, aryl or heterocyclic groups. The group —SH may also be referred to as "sulfhydryl" or "thiol" or "mercapto."

The term "tissue," as used herein, when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

The term "xanthophyll carotenoid," as used herein, generally refers to a naturally occurring or synthetic 40-carbon polyene chain with a carotenoid structure that contains at least one oxygen-containing functional group. The chain may include terminal cyclic end groups. Exemplary, though non-limiting, xanthophyll carotenoids include astaxanthin, zeaxanthin, lutein, echinenone, canthaxanthin, and the like. Non-limiting examples of carotenoids that are not xanthophyll carotenoids include β-carotene and lycopene.

Carotenoids and the Preparation and Use Thereof

Studies in cultured human cells have shown that lycopene 2F, the primary carotenoid in tomatoes, can be growth inhibitory against transformed cells as well as normal prostatic epithelium, alone and/or in combination with other antioxidants (e.g. vitamin E). In animal studies, the results regarding protection against proliferation of transformed cells induced with various carcinogenic agents have been positive. For example, in the ferret, the most representative model in terms of absorption-distribution-metabolism-excretion (ADME) for humans, lycopene was in fact protective against cigarette-smoke induced lung pathology. Epidemiological studies in humans clearly support an association between dietary consumption of lycopene-containing food products and a lower risk of prostate cancer. These lycopene-containing food products also contain lycophyll, albeit in lower relative amounts. In some cases, the natural dietary mixture of carotenoid compounds has efficacy in these settings, and synthetically-prepared or naturally-isolated lycopene does not. In some embodiments, a method of treating disease in a human subject may include administering to the human subject a pharmaceutical or nutraceutical composition including a predetermined ratio of one or more geometric and/or stereoisomers of a structural analog or derivative or synthetic intermediate of a carotenoid. In some embodiments, a method of treating disease in a human subject may include administering to the human subject a pharmaceutical or nutraceutical composition including a predetermined ratio of one or more structural analogs or derivatives or synthetic intermediates of a carotenoid. Prospective, randomized clinical trials in humans also demonstrate improved indices of proliferation and oxidative stress across a range of oral doses in cancer patients. Delivery of a highly potent radical scavenger to prostatic tissue may restore or augment endogenous antioxidant levels.

Lycoxanthin 2G and lycophyll 2H, which can be isolated from the red, ripe berries of *Solanum dulcamara*, as well as tomatoes and watermelon, are C40 lycopene-like xanthophylls functionalized with primary hydroxyl groups. The originally proposed chemical structures of the xanthophylls however lacked complete assignment and required further studies that were realized in the early 1970's. Utilizing high-resolution mass spectroscopy and NMR, the regiochemistry of the hydroxyl groups was characterized. Unambiguous confirmation of both structures were obtained approximately one year later, facilitated by the total syntheses of lycoxanthin and lycophyll reported by Kjøsen and Liaaen-Jensen in 1972. The original total synthesis was based on a C10+C20+C10 synthetic paradigm, in part due to the commercial availability of C20 dialdehyde (crocetindialdehyde). Up to the present, little additional chemical or biological information has accumulated in the primary literature for either compound.

In certain embodiments, carotenoids which may be synthesized using methods described herein may include carotenoids based on a chemical intermediate having the general structure

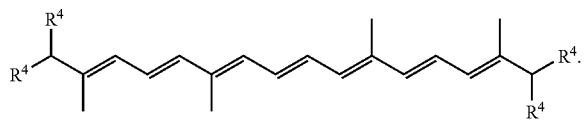

The compound depicted above embraces racemic, optically active stereoisomers and optically inactive stereoisomers. In some embodiments, $R^4$ may be $=O$, $OR^{11}$, $OsiR^{11}_3$, H, alkyl, or aryl. At least one R4 is $=O$ or $OR^{11}$. $R^{11}$ may be H, alkyl, or aryl. A method of synthesizing such a compound may include transforming a halogenated derivative having the general structure

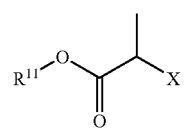

into a phosphorous compound having the general structure

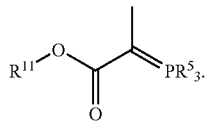

In some embodiments, $R^{11}$ may be alkyl or aryl. X may be a halogen (e.g., Br, Cl). The method may include reacting the phosphorous compound with an aldehyde or an aldehyde equivalent having a general structure

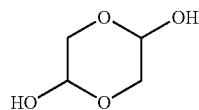

to form a alcohol coupling product having the general structure

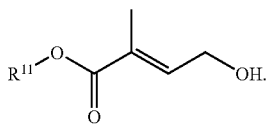

The method may include transforming the alcohol coupling product into a halogenated coupling product having the general structure

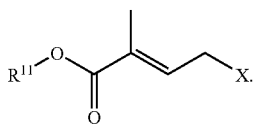

In some embodiments, $R^{11}$ may be alkyl or aryl. X may be a halogen (e.g., Br, Cl).

In some embodiments, a method may include transforming the halogenated coupling product into a phosphonium salt product product having the general structure

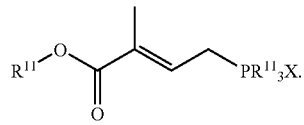

$R^{11}$ may be alkyl or aryl. X may be a halogen (e.g., Br, Cl).

In some embodiments, a method may include reacting the phosphonium salt product with a dialdehyde having the general structure

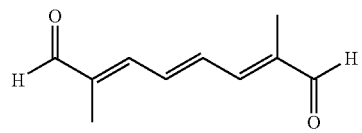

to form a carotenoid chemical intermediate having the general structure

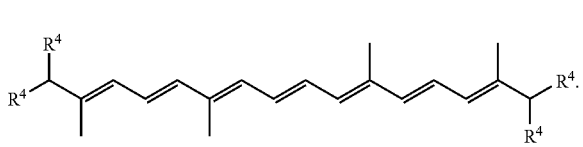

In some embodiments, $R^4$ may be =O, $OR^{11}$, $OsiR^{11}_3$, H, alkyl, or aryl. At least one R4 is =O or $OR^{11}$. $R^{11}$ may be H, alkyl, or aryl.

In some embodiments, a carotenoid chemical intermediate 214 may include a compound having the general structure

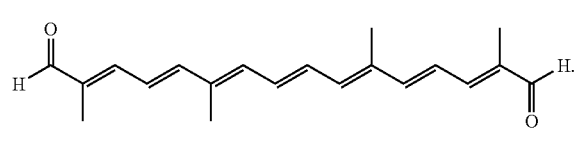

In some embodiments, a synthetic sequence used to produce C20 dialdehyde may include:

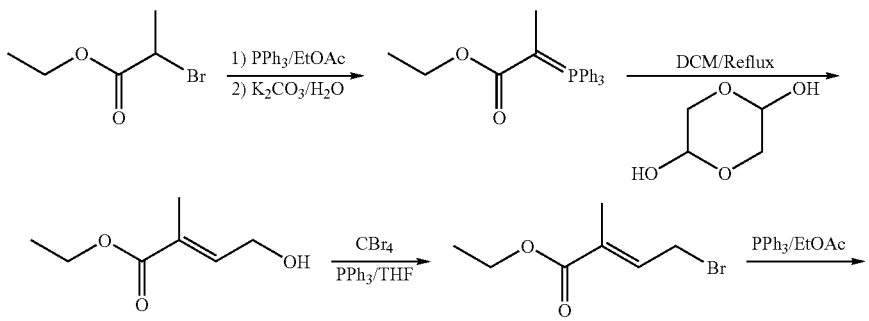

-continued

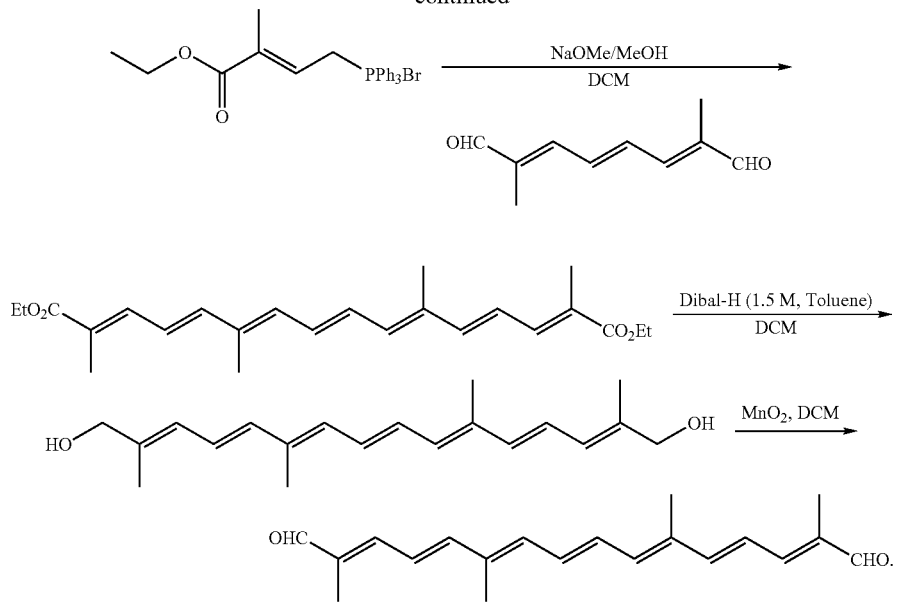

In some embodiments, carotenoid chemical intermediates may be used to synthesize naturally occurring carotenoids as well as carotenoid analogs and carotenoid derivatives. Carotenoid chemical intermediates may be used to synthesize naturally occurring carotenoids such as lycopene and lycophyll, and lycopene/lycophyll analogs and lycopene/lycophyll derivatives.

In some embodiments of a method to synthesize lycopene and lycophyll, and its derivatives and/or analogs, the chemical intermediate 214 pictured above having the general structure

214 may be coupled with a phosphonium salt product having the general structure to form lycopene having the general structure In some embodiments, Y may include —$CH_2$—$PR^{11}_3$ or —$CH_2$—$P(=O)(OR^{11})_2$. $R^{11}$ may be alkyl or aryl.

In some embodiments, methodologies as described herein (e.g., methods for synthesizing lycopene) may be used to prepare other acyclic carotenoids, as well as, derivatives and/or analogs of acyclic carotenoids. Of course it is understood that at least some of the intermediates used to synthesize acyclic carotenoids are also useful in the preparation of carotenoids containing cyclic rings (referred to herein sometimes as cyclic carotenoids, e.g., astaxanthin).

In some embodiments, a compound prepared by the method described herein may include an enantiomeric excess of at least one of the possible stereoisomers of the compound.

In some embodiments, a compound prepared by the method described herein may include an excess of a stereoisomer relative to the stereoisomer's statistical abundance.

In certain embodiments, carotenoids, carotenoid derivatives, or carotenoid analogs which may be synthesized using methods described herein may include carotenoids based on a chemical intermediate having the general structure

214

2F

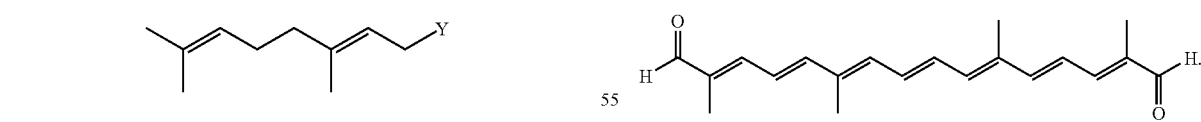

Compound 214 may be coupled to a phosphonium salt product 216 having the general structure

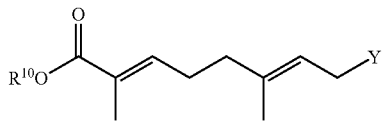

to form protected or masked carotenoid 218 having the general structure

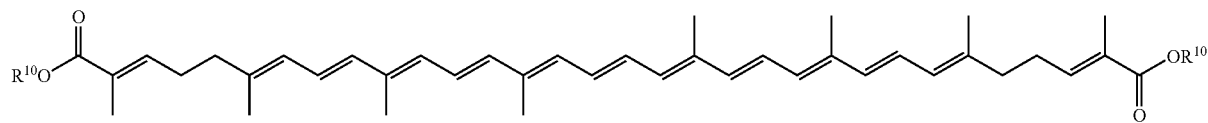

In some embodiments, Y may be $PR^{11}_3$ or $P(=O)(OR^{11})_2$. $R^{10}$ may be $SiR^{11}_3$, H, alkyl, or aryl. $R^{11}$ may be alkyl or aryl. In some embodiments, a solution of LiOMe (e.g., in methanol) may be used to couple the two compounds to prepare the protected or masked carotenoid.

In some embodiments of a method to synthesize lycopene and its derivatives and/or analogs, a phosphonium salt product having the general structure

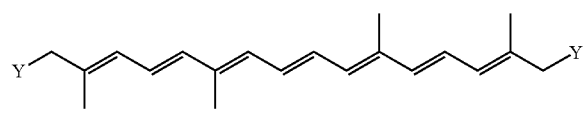

may be coupled with an aldehyde product having the general structure

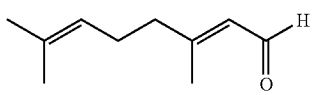

to form lycopene having the general structure

In some embodiments, Y may include $-CH_2-PR^{11}_3$ or $-CH_2-P(=O)(OR^{11})_2$. $R^{11}$ may be alkyl or aryl.

In some embodiments, a lycopene analog or a lycopene derivative may include one or more substituents. At least one of the substituents may include hydrophillic substituents. In some embodiments, substituents may include chemically reactive substituents which serve as chemical intermediates.

In some of the phosphonium salt product 216 embodiments, Y may be $PR^{11}_3$, $R^{11}$ may be phenyl, such that phosphonium salt product 216 has the general structure

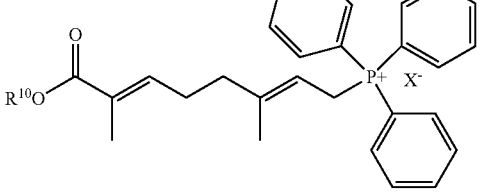

In some embodiments, X may be F, Cl, Br, or I. In some embodiments, $R^{10}$ may be methyl and X may be Br.

In some embodiments, a method may include reducing protected carotenoid 218 to form carotenoid 220 having the structure

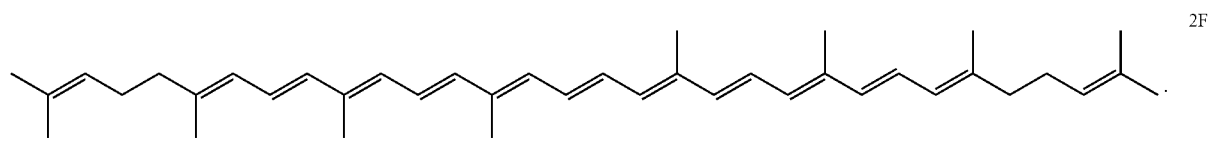

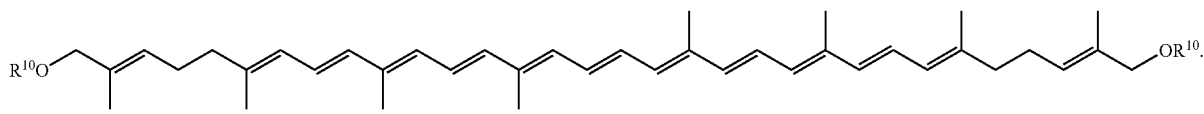

220

In some embodiments, $R^{10}$ may be $SiR^{11}{}_3$, H, alkyl, or aryl. $R^{11}$ may be alkyl or aryl. In some embodiments, $R^{10}$ may be H when protected carotenoid 218 is reduced. Reducing agents (e.g., DIBAL or Diisobutylaluminium hydride) known to one skilled in the art may be used to reduce the protected carotenoid 218 to form the carotenoid 220 where $R^{10}$ is H. Other reducing agents known to one skilled in the art may be used.

In some embodiment, a method may include preparing phosphonium salt product 216 by oxidizing ester 228 having the general structure

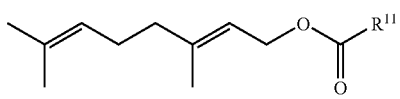

to form aldehyde 230 having the general structure

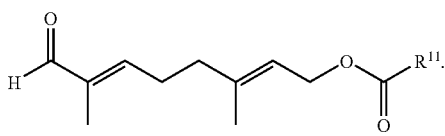

Selective oxidizing agents (e.g., $SeO_2$ in a solution of for example 95% ethanol) may be used to oxidize up to the aldehyde. The method may include oxidizing aldehyde 230 to form oxidized product 232 having the general structure

232

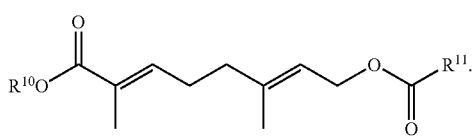

Selective oxidizing agents (e.g., $NaClO_2$, $Na_2HPO_4$, $Me_2C=CHMe$, t-BuOH/$H_2O$) may be used to oxidize up to the acid and/or ester. Oxidized product 232 may be selectively deprotected to form product 234 having the general structure

234

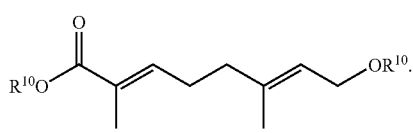

Selective bases (e.g., $K_2CO_3$, MeOH/$H_2O$) may be used to convert oxidized product 232 (e.g., to the alcohol and/or ether). Conversion of product 232 to product 234 may be viewed as more of a deprotection of an alcohol. The method may include halogenating product 234 to form halogenated product 236 having the general structure

236

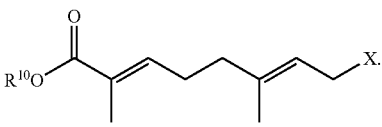

In an embodiment where product 234 includes an alcohol, halogenation of alcohols may be accomplished by a variety of methods (e.g., $CBr_4$/$Ph_3P$ in a polar solvent such as THF). Halogenated product 236 may be converted to the phosphonium salt product 216. Conversion of the halogen to the phosphonium salt may include using $Ph_3P$ in a solvent such as EtOAc. In some embodiments, X may be a counterion. X may include inorganic salts and/or organic salts. X may include F, Cl, Br, or I. $R^{10}$ may be $SiR^{11}{}_3$, H, alkyl, or aryl. $R^{11}$ may be alkyl, benzyl, or aryl.

In some embodiments, a multi-gram scale total synthesis of lycophyll (16,16'-dihydroxy-lycopene; ψ,ψ-carotene-16,16'-diol) may be based on a 2 (C10)+C20 synthetic methodology using the commercially available materials geraniol (C10) and crocetindialdehyde (C20). A late-stage double Wittig olefination of crocetindialdehyde may be used to form the lycophyll scaffold. The double Wittig may generate a mixture of polyenic geometric isomers that may be separated (e.g., using HPLC). The all-trans lycophyll may be achieved in >95% purity using about 8 linear synthetic steps. The disuccinate and diphosphate sodium salts of the rare carotenoid may then be prepared. Carotenoid derivatives and analogs (e.g., disuccinate and diphosphate sodium salts) may be readily dispersible in water without need for heat, detergents, co-solvents, or other additives. Retrometabolic in design, these novel derivatives could find utility in those applications where parenteral delivery of therapeutically relevant forms of lycophyll are desired.

Lycophyll was prepared by total synthesis at multiple gram scale for the current testing and derivatization to novel water-soluble, water-dispersible compounds. Isolation from natural sources demonstrates high cost, significant manpower, and generally low yields. Retrosynthetic analysis of the target xanthophyll revealed an efficient methodology utilizing at least some commercially available materials. In cases where commercial material was not available, these intermediates were synthesized in appropriate amounts. In some embodiments, commercially available materials may include geranyl acetate, a protected form of geraniol (C10), and/or crocetindialdehyde (C20). A method may include a total synthesis of acyclic carotenoids (e.g., lycophyll). In some embodiments, a synthesis of, for example, lycophyll may be realized in about 8 synthetic steps (Schemes 1 and 2). Synthetic steps may include an "endgame" double-Wittig olefination that successfully forms the target C40 scaffold while generating a mixture of geometric isomers (Scheme 2). The isomeric mixture may be deconvoluted to yield the target all-trans lycophyll. Deconvolution may include, but is not limited to, thermal or liquid chromatographic methods. The methodology shown in Schemes 1 and 2 for synthesizing lycophyll may be used to synthesize other acyclic carotenoids, carotenoid derivatives, and carotenoid analogs.

Scheme 1.
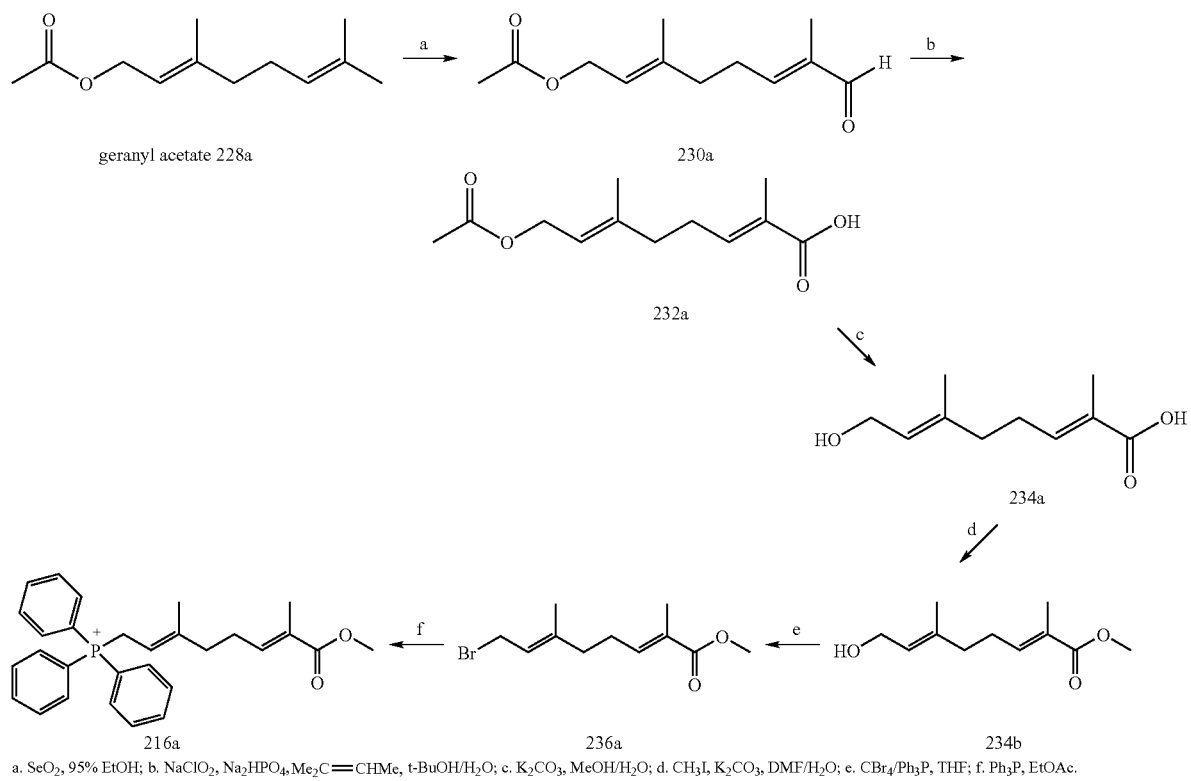
a. SeO$_2$, 95% EtOH; b. NaClO$_2$, Na$_2$HPO$_4$, Me$_2$C=CHMe, t-BuOH/H$_2$O; c. K$_2$CO$_3$, MeOH/H$_2$O; d. CH$_3$I, K$_2$CO$_3$, DMF/H$_2$O; e. CBr$_4$/Ph$_3$P, THF; f. Ph$_3$P, EtOAc.
Scheme 2.
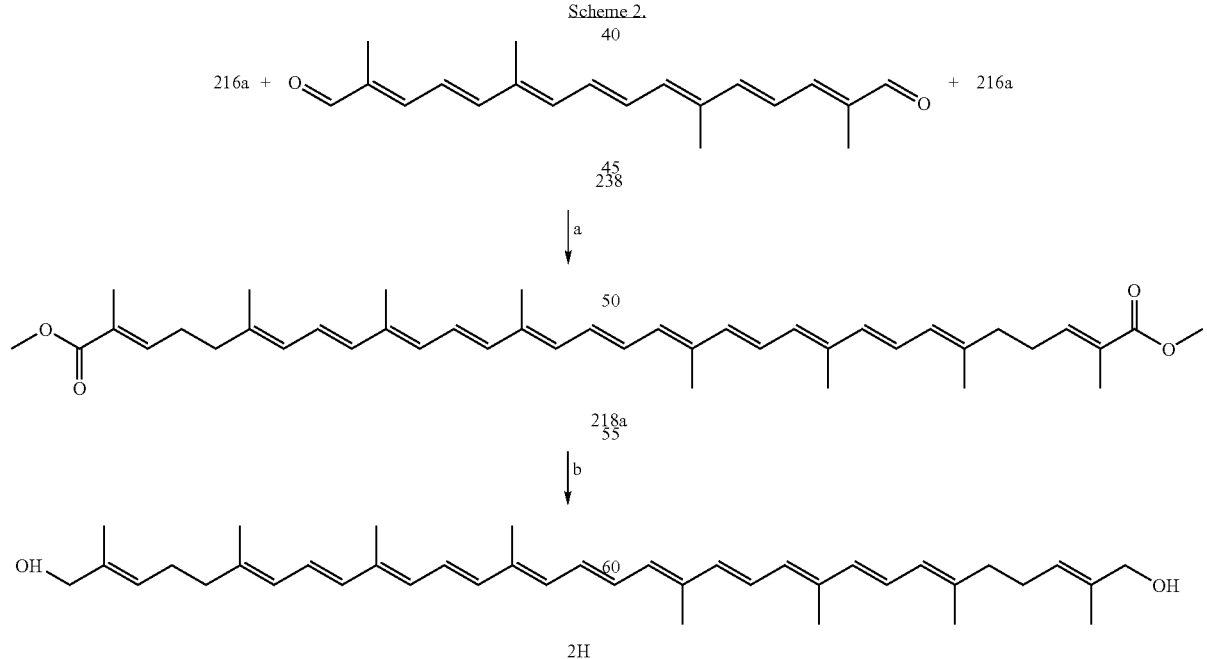
a. LiOMe in MeOH, toluene; b. DIBAL, THF.

In some embodiments, carotenoid chemical intermediates may be used to synthesize naturally occurring carotenoids such as xanthophylls. A method may include coupling a phosphonium salt product having the general structure

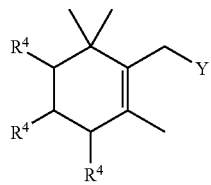

with a dialdehyde having the general structure

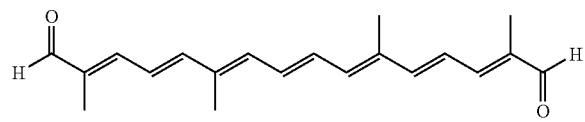

to form a carotenoid having the general structure

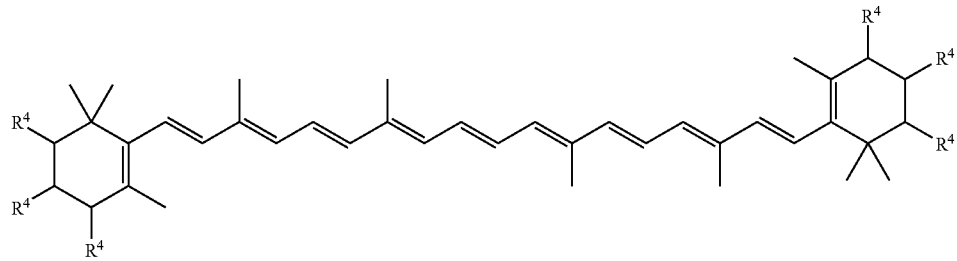

In some embodiments, $R^4$ may be H, =O, or $OR^{10}$. At least one R4 group is $OR^{10}$. $R^{10}$ may be $SiR^{11}{}_3$, H, alkyl, or aryl. $R^{11}$ may be alkyl or aryl. Y may include —$CH_2$—$PR^{11}{}_3$ or —$CH_2$—$P(=O)(OR^{11})_2$. Examples of xanthophyll carotenoids than may be synthesized using this methodology include, but are not limited to, astaxanthin, lutein, zeaxanthin, and canthaxanthin.

Research has shown that targeted derivatization of carotenoids can successfully increase the aqueous solubility and/or dispersibility of the highly lipophilic natural scaffolds. These compounds have demonstrated beneficial effects as direct aqueous radical scavengers, as myocardial salvage agents in experimental infarction models, as agents ameliorating and/or preventing chronic liver injury, and/or as cancer chemopreventive agents. The derivatives have shown increased utility as parenteral agents in these settings, as well as improved oral bioavailability in model animal studies.

In an embodiment, carotenoid derivatives may be synthesized from naturally-occurring carotenoids. The carotenoids may include structures 2A-2H depicted in FIG. 1. In some embodiments, the carotenoid derivatives may be synthesized from a naturally-occurring carotenoid including one or more alcohol substituents. In other embodiments, the carotenoid derivatives may be synthesized from a derivative of a naturally-occurring carotenoid including one or more alcohol substituents. The synthesis may result in a single stereoisomer. The synthesis may result in a single geometric isomer of the carotenoid derivative. The synthesis/synthetic sequence may include any prior purification or isolation steps carried out on the parent carotenoid.

In some embodiments, a synthesis may be a total synthesis using methods described herein to synthesize carotenoid derivatives and/or carotenoid analogs. Carotenoid derivatives and/or carotenoid analogs may include, but are not limited to, a 3S,3'S all-E carotenoid derivative, where the parent carotenoid is astaxanthin. The synthetic sequence may include protecting and subsequently deprotecting various functionalities of the carotenoid and/or substituent precursor. When derivates or analogs are prepared from alcohol functionalized carotenoids, a base catalyzed reaction may be used to react the alcohol functional groups with the substituent precursor. Substituent precursors include precursors that include a functional group that may act as a leaving group for a substitution reaction. The base may include any non-nucleophilic base known to one skilled in the art such as, for example, tertiary amines, pyridine, pyrrolidine, etc. The alcohol may act as a nucleophile reacting with the substituent precursor, displacing the leaving group. Leaving groups may include, but are not limited to, I, Cl, Br, tosyl, brosyl, mesyl, or trifyl. These are only a few examples of leaving groups that may be used, many more are known and would be apparent to one skilled in the art. In some embodiments, a base may be used to deprotonate the alcohol. For example, reaction with alkyl lithium bases, alkali metal hydroxide, or alkali metal alcohol salts may deprotonate a hydroxy group of the carotenoid. In other examples the leaving group may be internal and may subsequently be included in the final structure of the carotenoid derivative, a non-limiting example may include anhydrides or strained cyclic ethers. For example, the alcohol may be reacted with succinic anhydride.

In an embodiment, the disuccinic acid ester of astaxanthin may be further converted to the disodium salt. Synthetic sequences for the preparation of some of the specific embodiments depicted are described in the Examples section. The example depicted below is a generic non-limiting example of a synthetic sequence for the preparation of astaxanthin carotenoid derivatives.

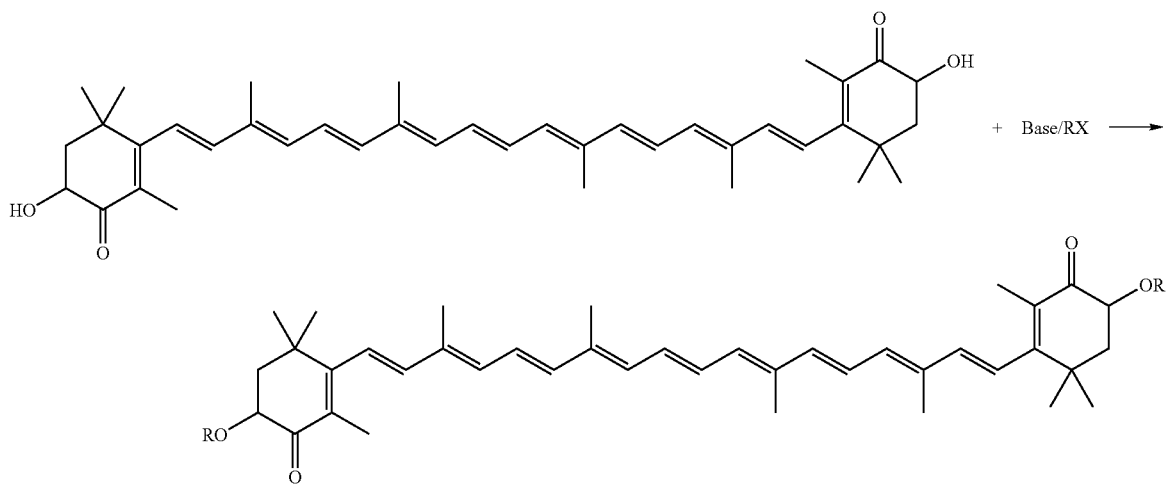

In some embodiments, carotenoid derivatives and analogs may be synthesized from naturally occurring carotenoids. These carotenoids may be synthetically produced and/or isolated from natural sources. Efforts have extended to include the derivatization of acyclic carotenoids (e.g., the rare xanthophyll lycophyll), specifically directed by principles of retrometabolic drug design.

In some embodiments, carotenoid analogs or derivatives may have increased water solubility and/or water dispersibility relative to some or all known naturally occurring carotenoids.

In some embodiments, carotenoid analogs or derivatives may be employed in "self-formulating" aqueous solutions, in which the compounds spontaneously self-assemble into macromolecular complexes. These complexes may provide stable formulations in terms of shelf-life. The same formulations may be parenterally administered, upon which the spontaneous self-assembly is overcome by interactions with serum and/or tissue components in vivo.

Water-soluble carotenoid analogs or derivatives may have a water solubility of greater than about 1 mg/mL in some embodiments. In certain embodiments, water-soluble carotenoid analogs or derivatives may have a water solubility of greater than about 5 mg/mL. In certain embodiments, water-soluble carotenoid analogs or derivatives may have a water solubility of greater than about 10 mg/mL. In certain embodiments, water-soluble carotenoid analogs or derivatives may have a water solubility of greater than about 20 mg/mL. In some embodiments, water-soluble carotenoid analogs or derivatives may have a water solubility of greater than about 50 mg/mL.

The synthesis of water-soluble and/or water-dispersible carotenoids (e.g., C40) analogs or derivatives—as potential parenteral agents for clinical applications may improve the injectability of these compounds as therapeutic agents, a result perhaps not achievable through other formulation methods. The methodology may be extended to carotenoids with fewer than 40 carbon atoms in the molecular skeleton and differing ionic character. The methodology may be extended to carotenoids with greater than 40 carbon atoms in the molecular skeleton. The methodology may be extended to non-symmetric carotenoids. The aqueous dispersibility of these compounds allows proof-of-concept studies in model systems (e.g. cell culture), where the high lipophilicity of these compounds previously limited their bioavailability and hence proper evaluation of efficacy. Esterification or etherification may be useful to increase oral bioavailability, a fortuitous side effect of the esterification process, which can increase solubility in gastric mixed micelles. These compounds, upon introduction to the mammalian GI tract, are rapidly and effectively cleaved to the parent, non-esterified compounds, and enter the systemic circulation in that manner and form. The effect of the intact ester and/or ether compound on the therapeutic endpoint of interest can be obtained with parenteral administration of the compound(s). The net overall effect is an improvement in potential clinical utility for the lipophilic carotenoid compounds as therapeutic agents.

In one embodiment, a subject may be administered a pharmaceutical composition comprising a carotenoid analog or derivative. The analog or derivative may be broken down according to the following reaction:

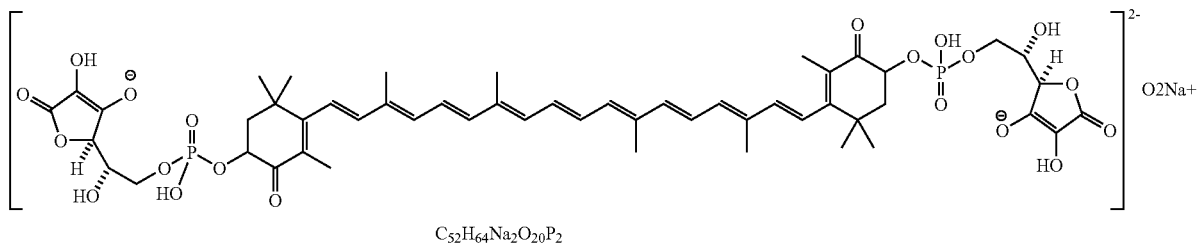

$C_{52}H_{64}Na_2O_{20}P_2$
Mol. Wt.: 1116.98

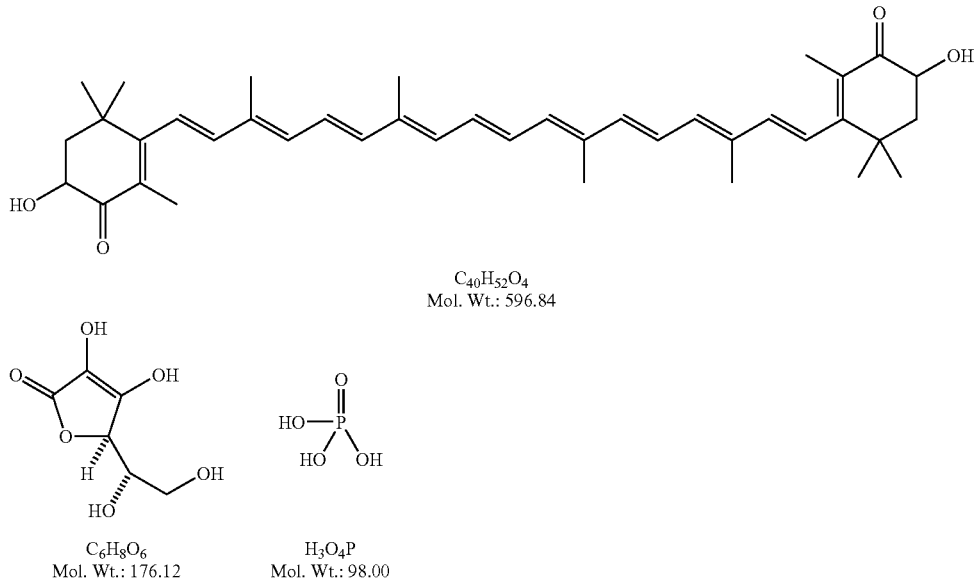

C40H52O4
Mol. Wt.: 596.84

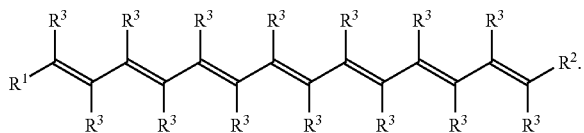

C6H8O6
Mol. Wt.: 176.12

H3O4P
Mol. Wt.: 98.00

Further details regarding the synthesis of carotenoid derivatives and analogs is illustrated in U.S. patent application Ser. No. 10/793,671 filed on Mar. 4, 2004, entitled "CAROTENOID ETHER ANALOGS OR DERIVATIVES FOR THE INHIBITION AND AMELIORATION OF DISEASE" by Lockwood et al. published on Jan. 13, 2005, as Publication No. US-2005-0009758 and U.S. patent application Ser. No. 11/106,378 filed on Apr. 14, 2005, entitled "CAROTENOID ANALOGS OR DERIVATIVES FOR THE INHIBITION AND AMELIORATION OF INFLAMMATION" to Lockwood et al. published on Nov. 24, 2005, as Publication No. U.S.-2005-0261254 both of which are incorporated by reference as though fully set forth herein.

Acquisition of lycophyll through total synthesis (Scheme 1 and 2) may facilitate the generation of water-dispersible acyclic carotenoid derivatives and analogs (e.g., lycophyll succinic and phosphoric diester salts (Scheme 3)). These compounds are readily dispersible in water without need of heat, detergents, co-solvents, or other additives. Such derivatives will likely find application in those indications in which parenteral delivery of highly-potent radical scavengers possessing an acyclic carotenoid (e.g., lycopene) scaffold are necessary to achieve their intended purpose. Specifically, these compounds may display efficacy in contemporary in vitro and in vivo cancer chemoprevention models, utilizing the natural tissue tropism of these compounds in mammals.

In some embodiments, a chemical composition may include one or more carotenoid analogs or derivatives having a general structure:

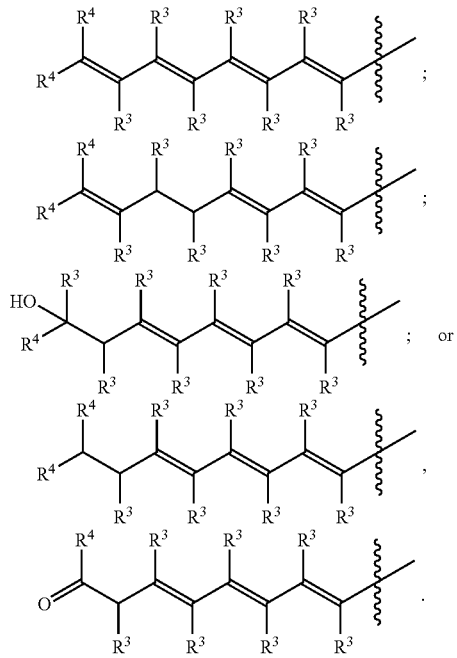

Each $R^3$ may be independently hydrogen or methyl. Each $R^1$ and $R^2$ may be independently:

Each $R^4$ may be independently hydrogen, —OH, —CH$_2$OH, or —OR$^5$. At least one $R^4$ group is —OR$^5$; wherein each $R^5$ is independently: alkyl; aryl; -alkyl-N(R$^7$)$_2$; -aryl-N(R$^7$)$_2$; -alkyl-N$^+$(R$^7$)$_3$; -aryl-N$^+$(R$^7$)$_3$; -alkyl-CO$_2$R$^7$; -aryl-CO$_2$R$^7$; -alkyl-CO$_2^-$; -aryl-CO$_2^-$; —CO$_2$R$^8$; —P(O)(OR$^8$)$_2$; —S(O)(OR$^8$)$_2$; an amino acid; a peptide, a carbohydrate; —C(O)—(CH$_2$)$_n$—CO$_2$R$^9$; a nucleoside residue, or a co-antioxidant. $R^7$ may be hydrogen, alkyl, or aryl. $R^8$ may be hydrogen, alkyl, aryl, benzyl or a co-antioxidant. $R^9$ may be hydrogen; alkyl; aryl; —P(O)(OR$^8$)$_2$; —S(O)(OR$^8$)$_2$; an amino acid; a peptide, a carbohydrate; a nucleoside; or a co-antioxidant. n may be 1 to 9.

In some embodiments, each $R^5$ may be independently: alkyl; aryl; $-P(O)(OR^8)_2$; an amino acid; a peptide, a carbohydrate; $-C(O)-(CH_2)_n-CO_2R^9$; a nucleoside residue, or a co-antioxidant. $R^8$ may be hydrogen, alkyl, aryl, benzyl or a co-antioxidant. $R^9$ may be hydrogen; alkyl; aryl; $-P(O)(OR^8)_2$; an amino acid; a peptide, a carbohydrate; a nucleoside, or a co-antioxidant. n may be 1 to 9.

In some embodiments, a chemical composition may include one or more carotenoid derivatives or analogs having the structure:

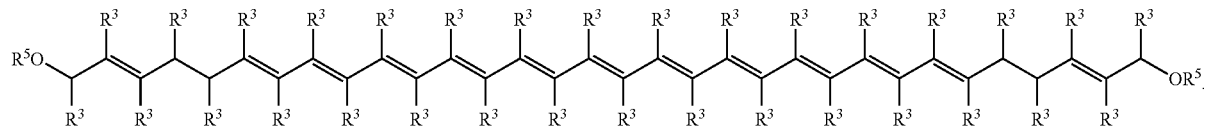

Each $R^3$ may be independently hydrogen or methyl. Each $R^5$ may be independently: alkyl; aryl; $-P(O)(OR^8)_2$; $-C(O)-(CH_2)_n-CO_2R^9$; or a co-antioxidant. $R^8$ may be hydrogen, alkyl, aryl, benzyl or a co-antioxidant. $R^9$ may be hydrogen; alkyl; aryl; $-P(O)(OR^8)_2$; or a co-antioxidant. n may be 1 to 9.

In some embodiments, a chemical composition may include one or more carotenoid derivatives or analogs having the structure:

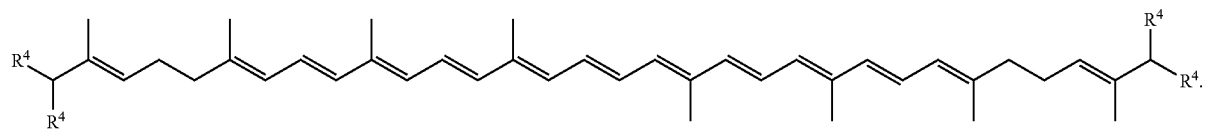

Each $R^4$ may be independently hydrogen, $-OH$, $-CH_2OH$, or $-OR^5$. At least one $R^4$ group is $-OR^5$. Each $R^5$ may be independently: alkyl; aryl; $-P(O)(OR^8)_2$; $-C(O)-(CH_2)_n-CO_2R^9$; or a co-antioxidant. $R^8$ may be hydrogen, alkyl, aryl, benzyl or a co-antioxidant. $R^9$ may be hydrogen; alkyl; aryl; $-P(O)(OR^8)_2$; or a co-antioxidant. n may be 1 to 9.

In some embodiments, a chemical composition may include one or more carotenoid derivatives or analogs having the structure:

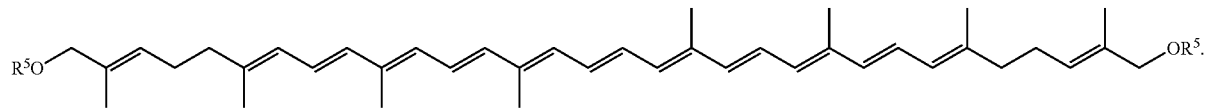

Each $-OR^5$ may be independently:

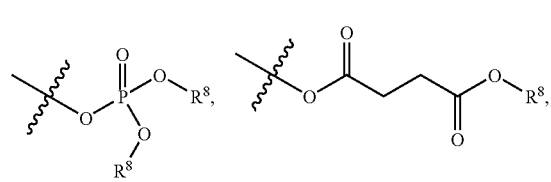

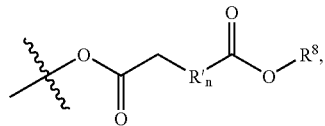

or a co-antioxidant. $R^8$ may be hydrogen, alkyl, aryl, benzyl, Group IA metal, or a co-antioxidant. R' may be $CH_2$. n may be 1 to 9.

In some embodiments, each $-OR^5$ may independently include:

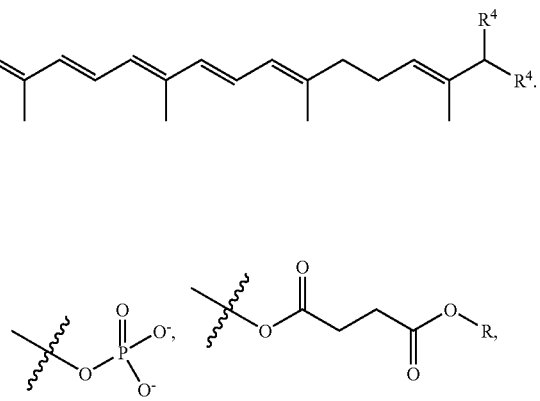

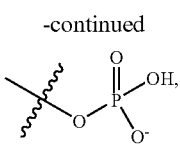

-continued

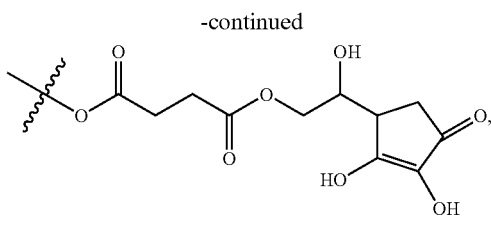

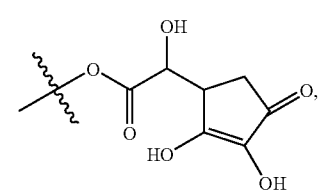

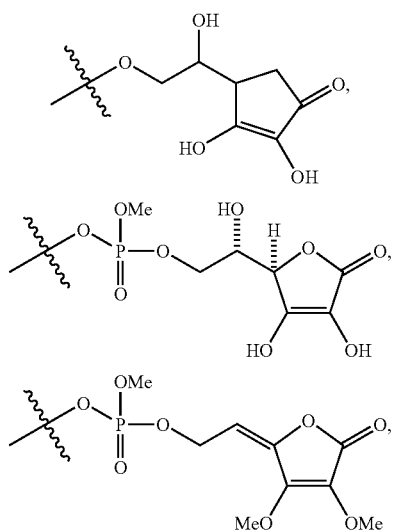

-continued

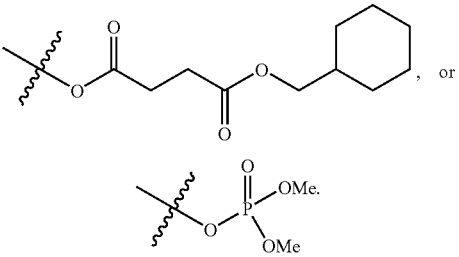

Each R may be independently H, alkyl, aryl, benzyl, Group IA metal, or co-antioxidant.

In some embodiments, each —$OR^5$ may independently include:

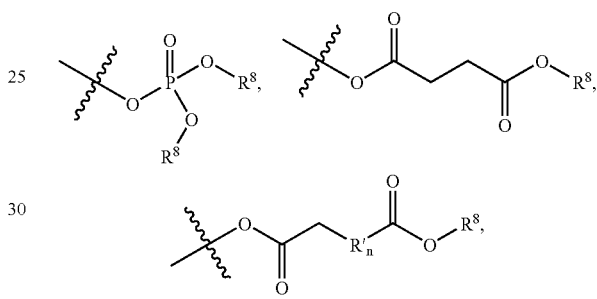

or a co-antioxidant. $R^8$ may be hydrogen, alkyl, aryl, benzyl, Group IA metal, or a co-antioxidant. R' may be $CH_2$. n may be 1 to 9.

In some embodiments, a composition may include one or more carotenoid derivatives or analogs having the structures:

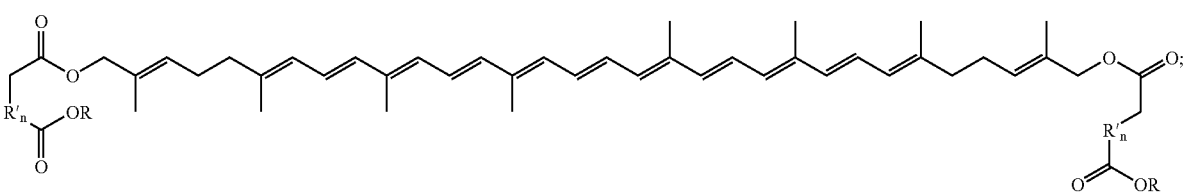

wherein each R is independently H, alkyl, aryl, benzyl, Group IA metal, or a co-antioxidant.

In some embodiments, a composition may include one or more carotenoid derivatives or analogs having the structures:

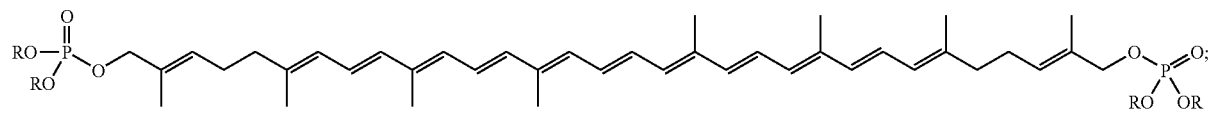

wherein each R is independently H, alkyl, aryl, benzyl, Group IA metal, or a co-antioxidant.

In some embodiments, a composition may include one or more carotenoid derivatives or analogs having the structures:

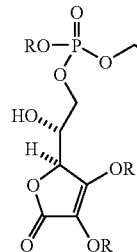

Each R may be independently H, alkyl, aryl, benzyl, or a Group IA metal.

In some embodiments, substituent $R^5$ in at least a portion of the carotenoid analogs or derivatives administered to the subject may be cleaved during use. The cleavage product may be biologically active. Cleavage of a carotenoid analog or derivative is carried out by one or more enzymes.

The absolute size of a carotenoid derivative (in 3 dimensions) is important when considering its use in biological and/or medicinal applications. Some of the largest naturally occurring carotenoids are no greater than about $C_{50}$. This is probably due to size limits imposed on molecules requiring incorporation into and/or interaction with cellular membranes. Cellular membranes may be particularly co-evolved with molecules of a length of approximately 30 nm. In some embodiments, carotenoid derivatives may be greater than or less than about 30 nm in size. In certain embodiments, carotenoid derivatives may be able to change conformation and/or otherwise assume an appropriate shape, which effectively enables the carotenoid derivative to efficiently interact with a cellular membrane. In some embodiments, a distance between $R^1$ and $R^2$ is between about 25 Å to about 55 Å. The distance between $R^1$ and $R^2$ is between about 40 Å to about 45 Å.

Some specific embodiments of carotenoid analogs or derivatives may include phosphate, succinate, co-antioxidant (e.g., Vitamin C, Vitamin C analogs, Vitamin C derivatives, Vitamin E, Vitamin E analogs, Vitamin E derivatives, or flavonoids), or combinations thereof derivatives or analogs of carotenoids. Flavonoids may include, for example, quercetin, xanthohumol, isoxanthohumol, or genistein. Vitamin E may generally be divided into two categories including tocopherols having a general structure

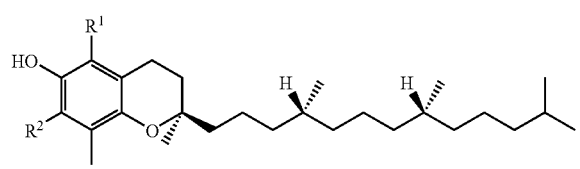

Alpha-tocopherol is used to designate when $R^1=R^2=CH_3$. Beta-tocopherol is used to designate when $R^1=CH_3$ and $R^2=H$. Gamma-tocopherol is used to designate when $R^1=H$ and $R^2=CH_3$. Delta-tocopherol is used to designate when $R^1=R^2=H$.

The second category of Vitamin E may include tocotrienols having a general structure

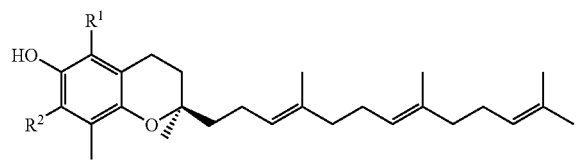

Alpha-tocotrienol is used to designate when $R^1=R^2=CH_3$. Beta-tocotrienol is used to designate when $R^1=CH_3$ and $R^2=H$. Gamma-tocotrienol is used to designate when $R^1=H$ and $R^2=CH_3$. Delta-tocotrienol is used to designate when $R^1=R^2=H$.

Quercetin, a flavonoid, has the structure

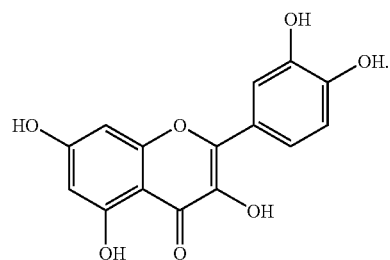

In some embodiments, a co-antioxidant may include Vitamin C, Vitamin C analogs, Vitamin C derivatives, Vitamin E, Vitamin E analogs, Vitamin E derivatives, flavonoids, flavonoid derivatives, or flavonoid analogs.

In some embodiments, flavonoids may include quercetin, xanthohumol, isoxanthohumol, or genistein.

In some embodiments, $R^5$ may include an amino acid derivative or a peptide. When $R^5$ is an amino acid derivative or a peptide, coupling of the amino acid or the peptide is accomplished through an ester linkage. The ester linkage may be formed between a free hydroxyl of the xanthophyll carotene and the carboxylic acid of the amino acid or peptide. When $R^9$ is an amino acid derivative or a peptide, coupling of the amino acid or the peptide is accomplished through an amide linkage. The amide linkage may be formed between the terminal carboxylic acid group of the linker attached to the xanthophyll carotene and the amine of the amino acid or peptide.

When $R^5$ is a sugar, $R^5$ includes, but is not limited to the following side chains:

—$CH_2$—$(CHOH)_n$—$CO_2H$;
—$CH_2$—$(CHOH)_n$—$CHO$;
—$CH_2$—$(CHOH)_n$—$CH_2OH$;
—$CH_2$—$(CHOH)_n$—$C(O)$—$CH_2OH$;

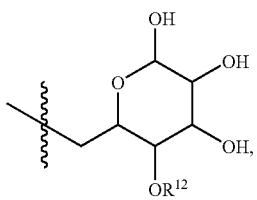

where $R^{12}$ is hydrogen or where $R^{13}$ is a purine or pyrimidine base, and $R^{12}$ is hydrogen or —OH.

In some embodiments, a composition may include a carotenoid analog or derivative that at least partially dissolves in water.

In some embodiments, one or more carotenoid derivatives or analogs may be synthetically derived.

In some embodiments, a method may include condensing an acyclic carotenoid (e.g., carotenoid 220) with succinic anhydride to prepare compound 222 having the general structure

222

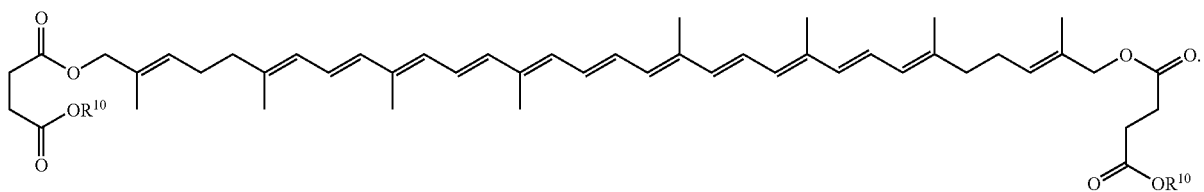

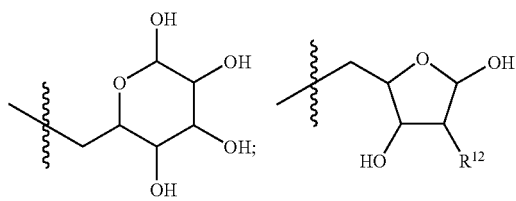

In some embodiments, $R^{10}$ may be $SiR^{11}_3$, H, alkyl, or aryl. $R^{11}$ may be alkyl or aryl. In some embodiments, $R^3$ may include a co-antioxidant (e.g., Vitamin C, Vitamin C analogs and derivatives) and/or other substituents described hererin. A base (e.g., N,N-diisopropylethylamine in a solvent (e.g., $CH_2Cl_2$)) may be used to facilitate condensation of carotenoid 220 with succinic anhydride. A non-nucleophilic base may be used. The method may include forming a salt 224 of compound 222 having a general structure

224

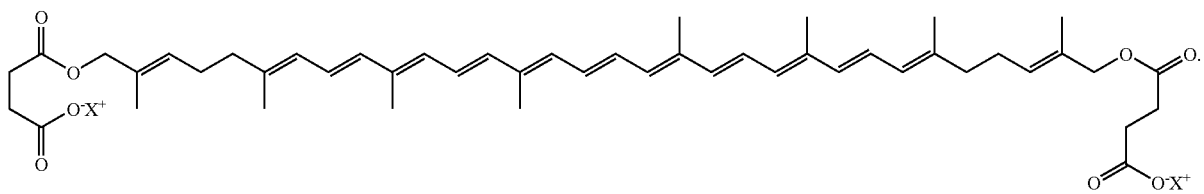

where $R^{13}$ is hydrogen or —OH.
When $R^5$ is a nucleoside, $R^5$ may have the structure:

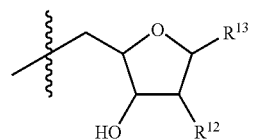

wherein X is a counterion. In some embodiments, X may be a counterion. X may include inorganic salts and/or organic salts. X may include, but is not limited to, Li, Na, or K. NaOMe may be used to convert the acid to the salt. Other reagents such as LiOMe, NaOEt, as well as other based may be used to prepare the salt.

In some embodiments, a method may include phosphorylating carotenoid 220 to form compound 226 having the general structure

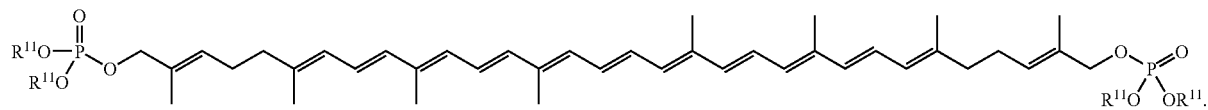

In some embodiments, $R^5$ may be H, alkyl, benzyl, or aryl. The method may include forming a salt 223 of compound 226 having a general structure limited to, Li, Na, or K. NaOMe may be used to convert the acid to the salt. Other reagents such as LiOMe, NaOEt, as well as other bases may be used to prepare the salt.

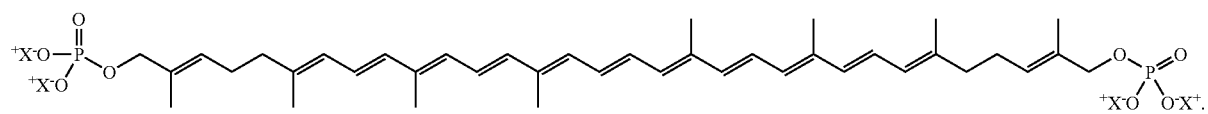

In some embodiments, X may be a counterion. X may include inorganic salts and/or organic salts. X may include, but is not

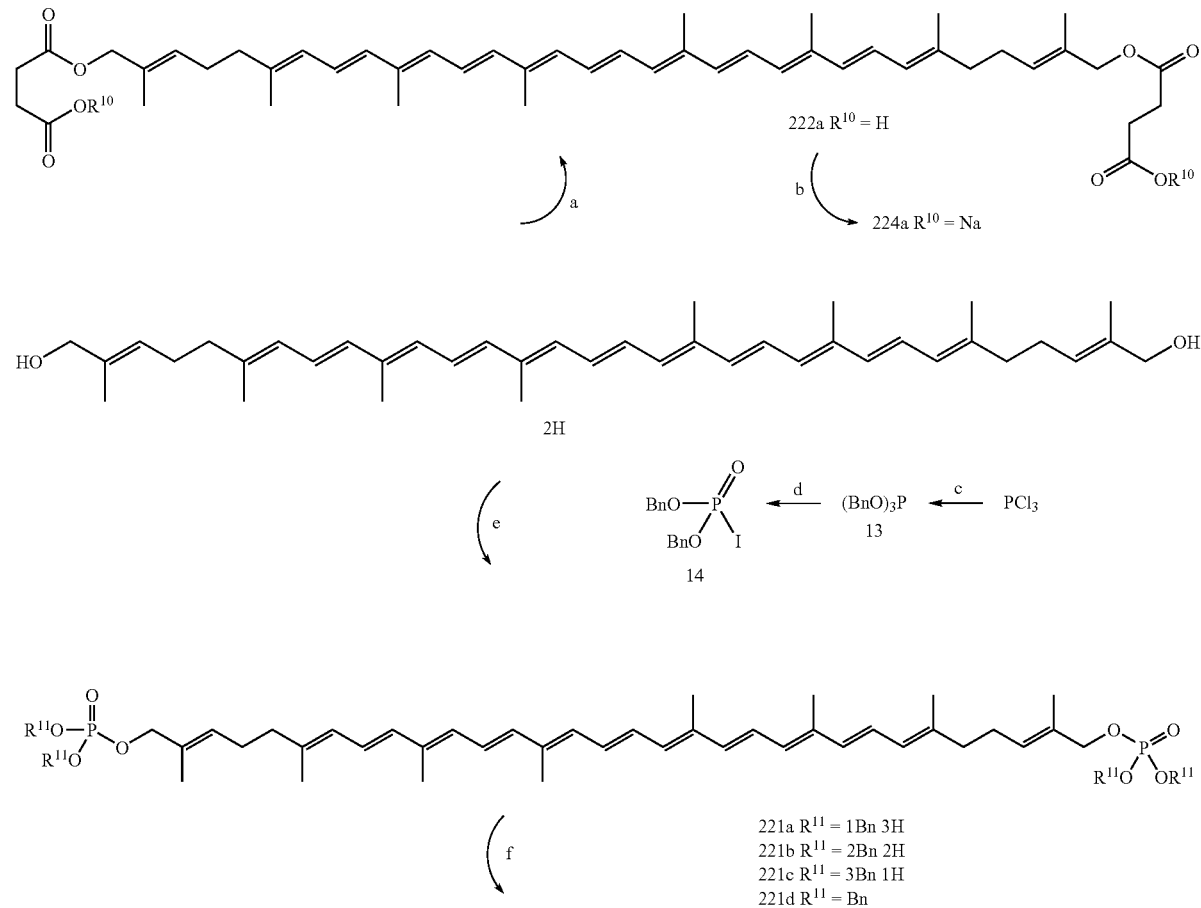

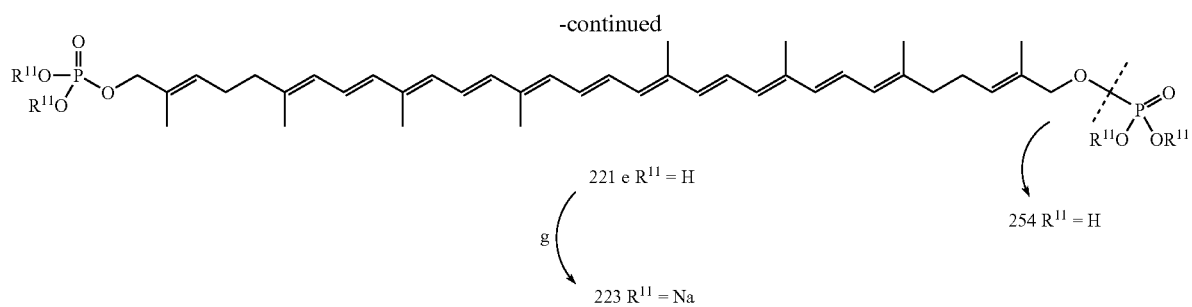

221 e R^{11} = H

223 R^{11} = Na

254 R^{11} = H a. succinic anhydride, N,N-diisopropylethylamine, $CH_2Cl_2$; b. NaOMe, $CH_2Cl_2$/MeOH (4/1); c. benzyl alcohol, triethylamine, $Et_2O$; d. $I_2$, $CH_2Cl_2$; e. pyridine, $CH_2Cl_2$, then 14; f. bromotrimethylsilane, N,O-bis(trimethylsilyl)acetamide, $CH_2Cl_2$ (254/222e (1/4), then reverse-phase HPLC; g. NaOMe, MeOH.

In some embodiments, one or more of the conversions and/or reactions discussed herein may be carried out within one reaction vessel increasing the overall efficiency of the synthesis of the final product. In some embodiments, a product of one reaction during a total synthesis may not be isolated and/or purified before continuing on with the following reaction. A reaction may instead only partially be worked up. For example, solid impurities which fall out of solution during the course of a reaction may be filtered off and the filtrate washed with solvent to ensure all of the resulting product is washed through and collected. In such a case the resulting collected product still in solution may not be isolated, but may then be combined with another reagent and further transformed. In some cases multiple transformations may be carried out in a single reaction flask simply by adding reagents one at a time without working up intermediate products. These types of "shortcuts" will improve the overall efficiency of a synthesis, especially when dealing with large scale reactions (e.g., along the lines of pilot plant scale and/or plant scale).

In some embodiments, the total synthesis of naturally-occurring carotenoids as starting scaffolds for carotenoid analogs or derivatives may be a method of generation of said carotenoid analogs or derivatives.

In some embodiments, it may be advantageous to be able to efficiently separate out individual stereoisomers of a racemic mixture of a chemical compound. Efficiently separating out individual stereoisomers on a relatively large scale may advantageously increase availability of starting materials.

In some embodiments, chromatographic separation techniques may be used to separate stereoisomers of a racemic mixture. In some embodiments pure optically active stereoisomers may be reacted with a mixture of stereoisomers of a chemical compound to form a mixture of diastereomers. Diastereomers may have different physical properties as opposed to stereoisomers, thus making it easier to separate diastereomers.

For example it may be advantageous to separate out stereoisomers from a racemic mixture of astaxanthin. In some embodiments, astaxanthin may be coupled to an optically active compound (e.g., dicamphanic acid). Coupling astaxanthin to optically active compounds produces diastereomers with different physical properties. The diastereomers produced may be separated using chromatographic separation techniques as described herein.

Dosage and Administration

The xanthophyll carotenoid, carotenoid derivative or analog may be administered at a dosage level up to conventional dosage levels for xanthophyll carotenoids, carotenoid derivatives or analogs, but will typically be less than about 2 gm per day. Suitable dosage levels may depend upon the overall systemic effect of the chosen xanthophyll carotenoids, carotenoid derivatives or analogs, but typically suitable levels will be about 0.001 to 50 mg/kg body weight of the patient per day, from about 0.005 to 30 mg/kg per day, or from about 0.05 to 10 mg/kg per day. The compound may be administered on a regimen of up to 6 times per day, between about 1 to 4 times per day, or once per day.

In the case where an oral composition is employed, a suitable dosage range is, e.g. from about 0.01 mg to about 100 mg of a xanthophyll carotenoid, carotenoid derivative or analog per kg of body weight per day, preferably from about 0.1 mg to about 10 mg per kg and for cytoprotective use from 0.1 mg to about 100 mg of a xanthophyll carotenoid, carotenoid derivative or analog per kg of body weight per day.

It will be understood that the dosage of the therapeutic agents will vary with the nature and the severity of the condition to be treated, and with the particular therapeutic agents chosen. The dosage will also vary according to the age, weight, physical condition and response of the individual patient. The selection of the appropriate dosage for the individual patient is within the skills of a clinician.

In some embodiments, compositions may include all compositions of 1.0 gram or less of a particular structural carotenoid analog, in combination with 1.0 gram or less of one or more other structural carotenoid analogs or derivatives or synthetic intermediates and/or co-antioxidants, in an amount which is effective to achieve its intended purpose. While individual subject needs vary, determination of optimal ranges of effective amounts of each component is with the skill of the art. Typically, a structural carotenoid analog or derivative or synthetic intermediates may be administered to mammals, in particular humans, orally at a dose of 5 to 100 mg per day referenced to the body weight of the mammal or human being treated for a particular disease. Typically, a structural carotenoid analog or derivative or synthetic intermediate may be administered to mammals, in particular humans, parenterally at a dose of between 5 to 1000 mg per day referenced to the body weight of the mammal or human being treated for a particular disease. In other embodiments, about 100 mg of a structural carotenoid analog or derivative or synthetic intermediate is either orally or parenterally administered to treat or prevent disease.

The unit oral dose may comprise from about 0.25 mg to about 1.0 gram, or about 5 to 25 mg, of a structural carotenoid analog. The unit parenteral dose may include from about 25 mg to 1.0 gram, or between 25 mg and 500 mg, of a structural carotenoid analog. The unit intracoronary dose may include from about 25 mg to 1.0 gram, or between 25 mg and 100 mg, of a structural carotenoid analog. The unit doses may be administered one or more times daily, on alternate days, in loading dose or bolus form, or titrated in a parenteral solution to commonly accepted or novel biochemical surrogate marker(s) or clinical endpoints as is with the skill of the art.

In addition to administering a structural carotenoid analog or derivative or synthetic intermediate as a raw chemical, the compounds may be administered as part of a pharmaceutical preparation containing suitable pharmaceutically acceptable carriers, preservatives, excipients and auxiliaries which facilitate processing of the structural carotenoid analog or derivative or synthetic intermediates which may be used pharmaceutically. The preparations, particularly those preparations which may be administered orally and which may be used for the preferred type of administration, such as tablets, softgels, lozenges, dragees, and capsules, and also preparations which may be administered rectally, such as suppositories, as well as suitable solutions for administration by injection or orally or by inhalation of aerosolized preparations, may be prepared in dose ranges that provide similar bioavailability as described above, together with the excipient. While individual needs may vary, determination of the optimal ranges of effective amounts of each component is within the skill of the art.

General guidance in determining effective dose ranges for pharmacologically active compounds and compositions for use in the presently described embodiments may be found, for example, in the publications of the International Conference on Harmonisation and in REMINGTON'S PHARMACEUTICAL SCIENCES, $8^{th}$ Edition Ed. Bertram G. Katzung, chapters 27 and 28, pp. 484-528 (Mack Publishing Company 1990) and yet further in BASIC & CLINICAL PHARMACOLOGY, chapters 5 and 66, (Lange Medical Books/McGraw-Hill, New York, 2001).

Pharmaceutical Compositions

Any suitable route of administration may be employed for providing a patient with an effective dosage of drugs of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In certain embodiments, it may be advantageous that the compositions described herein be administered orally.

The compositions may include those compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the drugs used in the present invention are conveniently delivered in the form of an aerosol spray presentation from pressurized packs or nebulisers. The compounds may also be delivered as powders which may be formulated and the powder composition may be inhaled with the aid of an insufflation powder inhaler device.

Suitable topical formulations for use in the present embodiments may include transdermal devices, aerosols, creams, ointments, lotions, dusting powders, and the like.

In practical use, drugs used can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the active compounds with solid and semi-solid excipients and suitable preservatives, and/or co-antioxidants. Optionally, the resulting mixture may be ground and processed. The resulting mixture of granules may be used, after adding suitable auxiliaries, if desired or necessary, to obtain tablets, softgels, lozenges, capsules, or dragee cores.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropylmethylcellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings, which, if desired, are resistant to gastric juices. Softgelatin capsules ("softgels") are provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or softgelatin capsules, for example, for identification or in order to characterize combinations of active compound doses, or to disguise the capsule contents for usage in clinical or other studies.

Other pharmaceutical preparations that may be used orally include push-fit capsules made of gelatin, as well as soft, thermally sealed capsules made of gelatin and a plasticizer such as glycerol or sorbitol. The push-fit capsules may contain the active compounds in the form of granules that may be mixed with fillers such as, for example, lactose, binders such as starches, and/or lubricants such as talc or magnesium stearate and, optionally, stabilizers and/or preservatives. In soft capsules, the active compounds may be dissolved or suspended in suitable liquids, such as fatty oils such as rice bran oil or peanut oil or palm oil, or liquid paraffin. In some embodiments, stabilizers and preservatives may be added.

In some embodiments, pulmonary administration of a pharmaceutical preparation may be desirable. Pulmonary administration may include, for example, inhalation of aerosolized or nebulized liquid or solid particles of the pharmaceutically active component dispersed in and surrounded by a gas.

Possible pharmaceutical preparations, which may be used rectally, include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration include, but are not limited to, aqueous solutions of the active compounds in water-soluble and/or water dispersible form, for example, water-soluble salts, esters, carbonates, phosphate esters or ethers, sulfates, glycoside ethers, together with spacers and/or linkers. Suspensions of the active compounds as appropriate oily injection suspensions may be administered, particularly suitable for intramuscular injection. Suitable lipophilic solvents, co-solvents (such as DMSO or ethanol), and/or vehicles including fatty oils, for example, rice bran oil or peanut oil and/or palm oil, or synthetic fatty acid esters, for example, ethyl oleate or triglycerides, may be used. Aqueous injection suspensions may contain substances that increase the viscosity of the suspension including, for example, sodium carboxymethyl cellulose, sorbitol, dextran, and/or cyclodextrins. Cyclodextrins (e.g., β-cyclodextrin) may be used specifically to increase the water solubility for parenteral injection of the structural carotenoid analog. Liposomal formulations, in which mixtures of the structural carotenoid analog or derivative with, for example, egg yolk phosphotidylcholine (E-PC), may be made for injection. Optionally, the suspension may contain stabilizers, for example, antioxidants such as BHT, and/or preservatives, such as benzyl alcohol.

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress or the development of a disease state.

By way of general guidance, the daily oral dosage of each active ingredient, when used for the indicated effects, will range between about 0.001 to 1000 mg/kg of body weight, between about 0.01 to 100 mg/kg of body weight per day, or between about 1.0 to 20 mg/kg/day. Intravenously administered doses may range from about 1 to about 10 mg/kg/minute during a constant rate infusion. Compounds of this invention may be administered in a single daily dose, or the total daily dosage may be administered in divided doses of two, three, or four or more times daily.

The pharmaceutical compositions described herein may further be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as "pharmacologically inert carriers") suitably selected with respect to the intended form of administration, that is, oral tablets, capsules, elixirs, syrups and the like, and consistent with conventional pharmaceutical practices.

For instance, for oral administration in the form of a tablet or capsule, the pharmacologically active component may be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams or more of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

EXAMPLES

Having now described the invention, the same will be more readily understood through reference to the following example(s), which are provided by way of illustration, and are not intended to be limiting of the present invention.

Example 1

Preparation of 2-(Triphenyl-phosphanylidene)-propionic acid ethyl ester

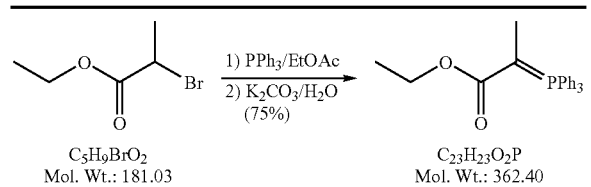

$C_5H_9BrO_2$
Mol. Wt.: 181.03

$C_{23}H_{23}O_2P$
Mol. Wt.: 362.40

| Raw Materials | FW | Quantity Used | Moles |
|---|---|---|---|
| Ethyl 2-bromopropionate | 181.03 | 1.0 Kg | 5.52 mol |
| Triphenyl Phosphine | 262.29 | 1.6 Kg | 6.10 mol |
| Potassium Carbonate | 138.21 | 800 g | 5.79 mol |

-continued

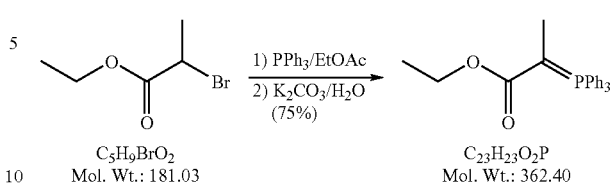

$C_5H_9BrO_2$
Mol. Wt.: 181.03

$C_{23}H_{23}O_2P$
Mol. Wt.: 362.40

| Raw Materials | FW | Quantity Used | Moles |
|---|---|---|---|
| EtOAc | | 10 L | |
| MeOH | | 10 L | |

1.6 Kg (6.10 mol) triphenyl phosphine was dissolved in 10 L ethyl acetate and 1.0 Kg of ethyl 2-bromopropionate was added into the above solution. The reaction mixture was stirred at room temperature for 2 days. White solid was filtered off and the precipitate was washed with ethyl acetate. The resulting compound was dissolved in methanol and treated with saturated aqueous potassium carbonate. After stirring for 2 h, the yellow solid was filtered off and washed with water to give 1.5 Kg (75%) of desired product.

Example 2

Preparation of 4-Hydroxy-2-methyl-but-2-enoic acid ethyl ester

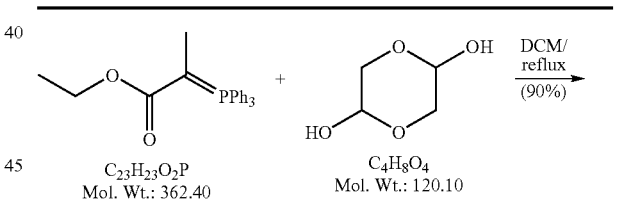

$C_{23}H_{23}O_2P$
Mol. Wt.: 362.40

$C_4H_8O_4$
Mol. Wt.: 120.10

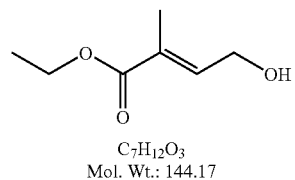

$C_7H_{12}O_3$
Mol. Wt.: 144.17

| Raw Materials | FW | Quantity Used | Moles |
|---|---|---|---|
| 2-(Triphenyl-phosphanylidene)-propionic acid ethyl ester | 362.40 | 886 g | 2.44 mol |
| Glycoaldehyde dimer | 120.10 | 140 g | 1.17 mol |
| DCM | | 10 L | |

886 g (2.44 mol) of 2-(triphenyl-phosphanylidene)-propionic acid ethyl ester in methylene chloride (4 L) was added dropwise into a refluxing solution of glycoaldehyde dimer (140 g, 1.17 mol) in methylene chloride (6 L). After refluxing for 4 h, the solvent was evaporated. Resulting crude product was fractionated (bp 108-114° C. at 2 mmHg) to give 304 g (90%) pure product as an oil. $^1$H-NMR (300 Hz CDCl$_3$) δ 6.88 (t, 1H, CH), 4.35 (d, 2H, CH$_2$OH), 4.20 (q, 2H, OCH$_2$), 1.85 (s, 3H, CH$_3$), 1.30 (t, 3H, CH$_3$).

Note: This process was repeated and 660 g title compound was collected.

Example 3

Preparation of 4-Bromo-2-methyl-but-2-enoic acid ethyl ester

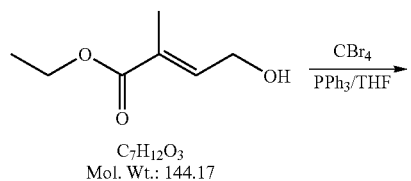

| Raw Materials | FW | Quantity Used | Moles |
|---|---|---|---|
| 4-Hydroxy-2-methyl-but-2-enoic acid ethyl ester | 144.17 | 567 g | 3.93 mol |
| Carbon tetrabromide | 331.63 | 1.44 kg | 4.34 mol |
| Triphenyl phosphine | 262.29 | 1.13 kg | 4.30 mol |
| THF | | 8 L | |

To a cooled solution (0° C.) of 4-hydroxy-2-methyl-but-2-enoic acid ethyl ester (567 g, 3.93 mol) in THF (8 L) was added carbon tetrabromide followed by triphenyl phosphine. The reaction mixture was slowly warmed to room temperature and stirred overnight. White solid (identified as compound 6) was isolated by filtering. The filtration was condensed and added ether, the resulting white precipitated (identified as triphenyl phosphate and triphenyl phosphine) was filtered off and discarded. Ether was evaporated and the resulting crude product was used without further purification in the next step.

Note: This process was repeated until 660 g of 4-hydroxy-2-methyl-but-2-enoic acid ethyl ester was consumed.

Example 4

Preparation of 2-Methyl-4-(triphenyl-phosphanyl)-but-2-enoic acid ethyl ester bromide salt

| Raw Materials | FW | Quantity Used | Moles |
|---|---|---|---|
| 4-Hydroxy-2-methyl-but-2-enoic acid ethyl ester | 207.07 | 940 g | 4.54 mol |
| Triphenyl phosphine | 262.29 | 1.34 Kg | 5.11 mol |
| EtOAc | | 10 L | |

940 g (4.54 mol) of 4-hydroxy-2-methyl-but-2-enoic acid ethyl ester was added into the solution of triphenyl phosphine (1.34 Kg, 5.11 mol) in 10 L ethyl acetate. The reaction mixture was stirred at room temperature for 2 days. The resulting white precipitate was filtered and washed with ethyl acetate to give 2.11 kg (99%) of the title compound. $^1$H-NMR (300 Hz DMSO-d$_6$) δ 7.78-7.95 (m, 15H, ArH), 6.40 (q, 1H, CH), 4.76 (q, 2H, CH$_2$P), 4.10 (q, 2H, CH$_2$), 1.60 (d, 3H, CH$_3$), 1.15 (t, 3H, CH$_3$).

Note: This process was repeated and 4.2 Kg title compound was collected

Example 5

Preparation of 2,6,11,15-Tetramethyl-hexadeca-2,4,6,8,10,12,14-heptaenedioic acid diethyl ester

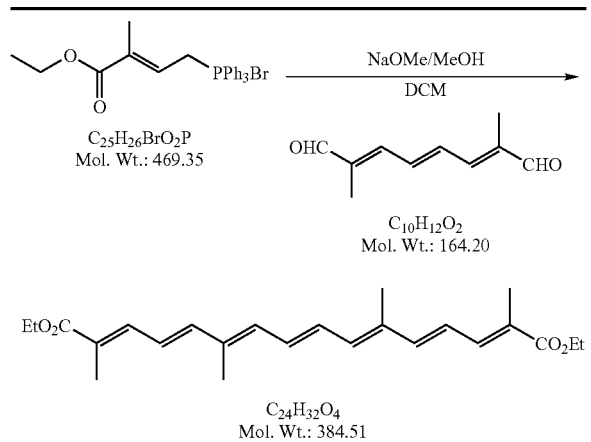

| Raw Materials | FW | Quantity Used | Moles |
|---|---|---|---|
| 2-Methyl-4-(triphenyl-phosphanyl)-but-2-enoic acid ethyl ester bromide salt | 469.35 | 2006.6 g | 4.28 mol |
| 2,7-Dimethyl-octa-2,4,6-trienedial | 164.20 | 234 g | 1.43 mol |
| NaOMe/MeOH (30%) | 54.02 | 749 mL | 4.00 mol |
| Methylene chloride | | 5 L | |

To a refluxing solution of 2-Methyl-4-(triphenyl-phosphanyl)-but-2-enoic acid ethyl ester bromide salt (2006.6 g, 4.28 mol) and 2,7-Dimethyl-octa-2,4,6-trienedial (234 g, 1.43 mol) in DCM (5 L) was added dropwise a solution of 30% by wt. NaOMe (749 mL, 4.00 mol) in methanol. The reaction mixture was refluxed for 3 hrs. The mixture was pushed through a short column of silica and the solvent was reduced in vacuo. The residue was redissolved in EtOH (3 L) and heated to reflux for 3 hrs. Cooled and filtered. The solid was washed with MeOH (100 mL×3) then diethyl ether (100 mL) and dried to give 250 g of orange powder (45%) $^1$H NMR (300 Hz, CDCl$_3$) δ 7.28 (s, 1H, CH), 7.26 (s, 1H, CH), 6.60 (m, 8H, CH), 4.23 (q, 4H, CH$_2$), 1.98 (s, 6H, CH$_3$), 1.53 (s, 6H, CH$_3$), 1.25 (t, 6H, CH$_3$).

Example 6

Preparation of 2,6,11,15-Tetramethyl-hexadeca-2,4,6,8,10,12,14-heptaene-1,16-diol

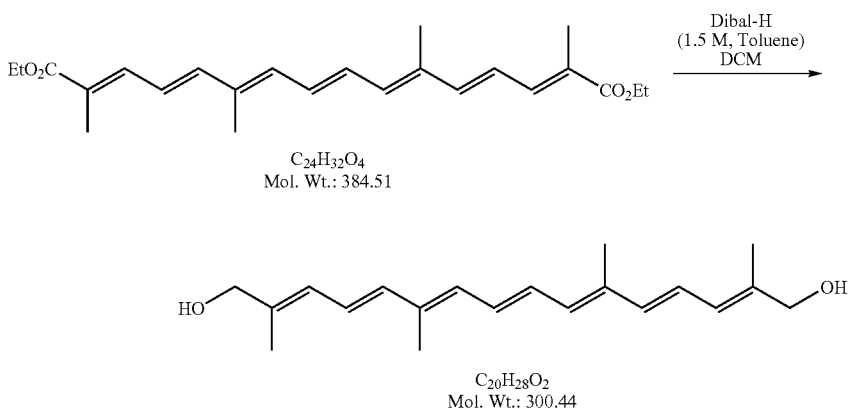

| Raw Materials | FW | Quantity Used | Moles |
|---|---|---|---|
| 2,6,11,15-Tetramethyl-hexadeca-2,4,6,8,10,12,14-heptaenedioic acid diethyl ester | 384.51 | 200 g | 0.52 mol |
| Methylene chloride | | 3000 mL | |
| Diisobutylaluminum hydride-(1.5 M, Toluene) | 142.22 | 1533 mL | 2.30 mol |

To a solution of 2,6,11,15-tetramethyl-hexadeca-2,4,6,8,10,12,14-heptaenedioic acid diethyl ester (200 g, 0.52 mol) in 3000 mL of DCM was added dropwise a solution of diisobutylaluminum hydride in toluene (1.5 M, 1533 mL, 2.30 mol) at −78° C. The mixture was stirring at 0° C. for 2 h. 100 mL of water was added the 200 ml of 2N NaOH was added to quench the reaction. The suspension was filtered off and solid was washed by a large amount of THF. The combined organic layer were dried over $Na_2SO_4$ and evaporated to give 133.16 g (85%) brown solid. $^1$H NMR (300 Hz, $CDCl_3$) δ 6.41 (m, 10H, CH), 4.16 (s, 4H, $CH_2$), 1.95 (m, 12H, $CH_3$)

Example 7

Preparation of 2,6,11,15-Tetramethyl-hexadeca-2,4,6,8,10,12,14-heptaenedial

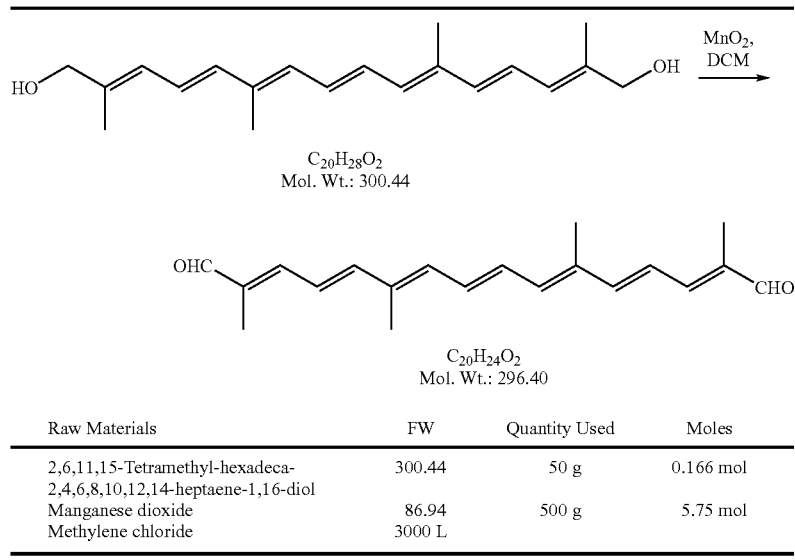

| Raw Materials | FW | Quantity Used | Moles |
| --- | --- | --- | --- |
| 2,6,11,15-Tetramethyl-hexadeca-2,4,6,8,10,12,14-heptaene-1,16-diol | 300.44 | 50 g | 0.166 mol |
| Manganese dioxide | 86.94 | 500 g | 5.75 mol |
| Methylene chloride | 3000 L | | |

To a suspension of 2,6,11,15-tetramethyl-hexadeca-2,4,6,8,10,12,14-heptaene-1,16-diol (50 g, 0.166 mol) in 3000 mL of DCM was added portionwise manganese dioxide (500 g, 5.75 mol) at room temperature. The mixture was After heated to reflux for 2 h, the solid was filtered via celite and washed with $CH_2Cl_2$. The solvent was removed under reduced pressure to give 36 g of pure product (73%). $^1$H-NMR (300 Hz DMSO-$d_6$) δ 9.42 (s, 2H, CHO), 7.18 (s, 1H, CH), 7.16 (s, 1H, CH), 6.93 (m, 6H, CH), 2.01 (s, 6H, $CH_3$), 1.82 (s, 6H, $CH_3$).

Example 8

General Preparation of Lycophyll 2H

Crocetindialdehyde (238) was obtained from SynChem, Inc. (Des Plaines, Ill.) as a brick-red solid and was used without further purification. Lycopene was obtained from ChromaDex (Santa Ana, Calif.) as a red solid and was used without further purification. Acetic acid 3,7-dimethyl-8-oxo-octa-2,6-dienyl ester (230a) (Liu and Prestwich 2002) was synthesized by literature procedures from commercially available geranyl acetate (228a). All other reagents and solvents used were purchased from Acros Organics (Morris Plains, N.J.) and Sigma-Aldrich (St. Louis, Mo.) and were used without further purification. All reactions were performed under a nitrogen atmosphere. All flash chromatographic purifications were performed on Natland International Corporation 230-400 mesh silica gel using indicated solvents. LC/MS (APCI and ESI+ modes) were recorded on an Agilent 1100 LC/MSD VL system; column: Zorbax Eclipse XDB-C18 Rapid Resolution (4.6×75 mm, 3.5 μm); temperature: 25° C.; flow rate: 1.0 mL/min.; mobile phase (A=0.025% TFA in $H_2O$, B=0.025% TFA in acetonitrile). Gradient program (for intermediates 230a-236a and 216a): 70% A/30% B (start), step gradient to 50% B over 5 minutes, step gradient to 100% B over 1.3 minutes, hold at 100% B over 4.9 minutes. Gradient program (for intermediates 218a, 2H): 70% A/30% B (start), step gradient to 50% B over 5 minutes, step gradient to 98% B over 3.3 minutes, hold at 98% B over 16.9 minutes. All-trans lycophyll was obtained from crude material using a Waters 996 Photo Diode Array detector, Millipore 600E System Controller and Waters 717 Autosampler; column: YMC C30 Carotenoid S-5, (10×250 mm, 5 μm column); temperature: 25° C.; flow rate: 4.7 mL/min; mobile phase (A=methanol (MeOH), B=methyl-t-butyl ether (MTBE)) Gradient program: 60% A/40% B (start), step gradient to 80% A over 1 minute, hold at 80% A over 119 minutes. Fractions were collected from 55-66 minutes. Fraction analysis was performed on a YMC C30 Carotenoid S-5, (4.6×250 mm, 5 μm column). Proton nuclear magnetic resonance (NMR) spectra were obtained on a Varian Unity INOVA 500 spectrometer operating at 500.111 MHz (megahertz). Electronic absorption spectra were recorded on a Cary 50 Bio UV-Visible spectrophotometer.

Example 9

Preparation of 8-Acetoxy-2,6-dimethyl-octa-2,6-dienoic acid (232a)

To a solution of aldehyde 230a (19.5 g, 92.7 mmol) in 300 mL of tert-butyl alcohol was added 2-methyl-2-butene (98.0 mL, 925 mmol). To this was added a solution of sodium dihydrogen phosphate (44.5 g, 371 mmol) in 300 mL of water. Sodium chlorite (33.6 g, 371 mmol) was added in several portions. The resulting mixture was rapidly stirred overnight at room temperature. Ethyl acetate was added and the aqueous layer was acidified to pH 3 by addition of 1 M HCl. The organic layer was separated, and the aqueous layer was extracted with ethyl acetate (3×200 mL). The combined organic extracts were washed with brine, dried over MgSO$_4$, and reduced to dryness in vacuo. The crude product (27.4 g, 121 mmol, >100% yield) was used in the next step without further purification:
$^1$H NMR (500 MHz, CDCl$_3$) δ: 6.84(t of q, J=7.25 Hz, J=1.50 Hz, 1H, =CH), 5.34 (t of q, J=7.00 Hz, J=1.50 Hz, 1H, =CH), 4.56 (d, J=7.00 Hz, 2H, —CH$_2$O—), 2.31 (q, J=7.50 Hz, 2H, —CH$_2$—), 2.15 (t, J=7.50 Hz, 2H, —CH$_2$—), 2.03 (s, 3H, —CH$_3$), 1.81 (s, 3H, —CH$_3$), 1.70 (s, 3H, —CH$_3$). LC/MS (ESI): m/z 249 [M+Na]$^+$.

Example 10

Preparation of 8-Hydroxy-2,6-dimethyl-octa-2,6-dienoic acid (234a)

To a solution of acid 232a (20.0 g, 88.4 mmol) in 400 mL of methanol was added a solution of potassium carbonate (24.4 g, 177 mmol) in 100 mL of water. The resulting mixture was vigorously stirred overnight at room temperature. The reaction was cooled to 0° C., methylene chloride (200 mL) was added, and the aqueous layer was acidified to pH 3 with 1 M HCl. The organic layer was separated, and the aqueous layer was extracted with methylene chloride (2×200 mL). The combined organic extracts were washed with brine, dried over MgSO$_4$, and reduced to dryness in vacuo. The crude product (9.65 g, 52.4 mmol, 59% yield) was used in the next step without further purification: $^1$H NMR (500 MHz, CDCl$_3$) δ: 6.86 (t of q, J=7.25 Hz, J=1.50 Hz, 1H, =CH), 5.43 (t of q, J=7.00 Hz, J=1.50 Hz, 1H, =CH), 4.16 (d, J=7.00 Hz, 2H, —CH$_2$O—), 2.33(q, J=7.50 Hz, 2H, —CH$_2$—), 2.16 (t, J=7.50 Hz, 2H, —CH$_2$—), 1.83 (s, 3H, —CH$_3$), 1.68 (s, 3H, —CH$_3$). LC/MS (ESI): m/z 207 [M+Na]$^+$.

Example 11

Preparation of 8-Hydroxy-2,6-dimethyl-octa-2,6-dienoic acid methyl ester (234b)

To a solution of acid 234a (20.1 g, 109 mmol) in 400 mL of DMF was added a solution of potassium carbonate (16.6 g, 120 mmol) in 80 mL of water. The resulting mixture was vigorously stirred for several minutes. To the mixture was added iodomethane (7.50 mL, 120 mmol) via syringe. The resulting mixture was vigorously stirred overnight at room temperature. Ethyl acetate (400 mL) and water (400 mL) were added and the aqueous layer was acidified to pH 3 by addition of 1 M HCl. The organic layer was separated and the aqueous layer was extracted with ethyl acetate (3×200 mL). The combined organic extracts were washed with water (3×500 mL), saturated aqueous sodium carbonate, brine, and dried over MgSO$_4$. The solvent was removed under reduced pressure and the crude product purified by flash chromatography (MeOH/CH$_2$Cl$_2$, 1:49) to afford methyl ester 5 as a clear oil (19.4 g, 90% yield): $^1$H NMR (500 MHz, CDCl$_3$) δ: 6.72 (t of q, J=7.50 Hz, J=1.50 Hz, 1H, =CH), 5.43 (t of q, J=6.75 Hz, J=1.50 Hz, 1H, =CH), 4.16 (d, J=7.00 Hz, 2H, —CH$_2$O—), 3.73 (s, 3H, —CH$_3$), 2.31 (q, J=7.50 Hz, 2H, —CH$_2$—), 2.15 (t, J=7.50 Hz, 2H, —CH$_2$—), 1.83 (s, 3H, —CH$_3$), 1.69 (s, 3H, —CH$_3$). LC/MS (ESI): m/z 221 [M+Na]$^+$.

Example 12

Preparation of 8-Bromo-2,6-dimethyl-octa-2,6-dienoic acid methyl ester (236a)

To a 0° C. solution of alcohol 234b (12.9, 64.9 mmol) in 250 mL of anhydrous tetrahydofuran was added carbon tetrabromide (23.8 g, 71.4 mmol) in several portions. The mixture was stirred for a few minutes and then triphenylphosphine (18.7 g, 71.4 mmol) was added and the mixture allowed to warm to room temperature and stirred overnight. The solvent was removed under reduced pressure and the resulting residue was suspended in diethyl ether. The suspension was filtered through a pad of Celite. After solvent removal under reduced pressure the resulting crude product (contaminated with triphenylphosphine oxide) was used directly in the next step: $^1$H NMR (500 MHz, CDCl$_3$) δ: 6.61 (t of q, J=7.50 Hz, J=1.50 Hz, 1H, =CH), δ 47 (t of q, J=8.00 Hz, J=1.50 Hz, 1H, =CH), 3.92 (d, J=8.50 Hz, 2H, —CH$_2$Br), 3.63 (s, 3H, —CH$_3$), 2.22 (q, J=8.00 Hz, 2H, —CH$_2$—), 2.10 (t, J=8.00 Hz, 2H, —CH$_2$—), 1.75 (d, J=1.00 Hz, 3H, —CH$_3$), 1.66 (d, J=1.00 Hz, 3H, —CH$_3$).

Example 13

Preparation of (2,6-Dimethyl-8-octa-2,6-dienoic acid methyl ester)triphenylphosphonium bromide (216a)

To a solution of bromide 236a (9.20 g, 35.2 mmol) in ethyl acetate (200 mL) was added triphenylphosphine (10.2 g, 38.8 mmol). The resulting mixture was vigorously stirred for a few minutes, at which time an insoluble material began to oil out from the solution, adhering to the sides of the flask. The reaction solution was then decanted into a clean reaction vessel. This procedure was repeated every 5 to 10 minutes until no more oily insoluble residue was noted, at which time a white solid started to precipitate from the solution. The cloudy mixture was then stirred overnight at room temperature. The mixture was filtered and the filter cake was rinsed with ethyl acetate and dried in vacuo to afford phosphonium salt 7 as a white solid (9.60 g, 52% yield). $^1$H NMR (500 MHz, CDCl$_3$) δ: 7.88-7.84 (m, 6 arom. H), 7.79-7.75 (m, 3 arom. H), 7.68-7.64 (m, 6 arom. H), 6.51 (t of q, J=5.00 Hz, J=1.00 Hz, 1H, =CH), 5.10 (q, J=7.00 Hz, 1H, =CH), 4.70 (d of d, J=15.0, J=8.00 Hz, 2H, —CH$_2$PPh$_3$Br), 3.67 (s, 3H, —CH$_3$), 2.16 (q, J=7.00 Hz, 2H, —CH$_2$—), 2.08 (t, J=6.00 Hz, 2H, —CH$_2$—), 1.70 (s, 3H, —CH$_3$), 1.35 (d, J=4.00 Hz, 3H, —CH$_3$). LC/MS (ESI): m/z 443 [M]$^+$.

Example 14

Preparation of Dimethyl ψ,ψ-Carotene-16,16'-dioate (218a)

To a solution of crocetindialdehyde (238) (0.810 g, 2.74 mmol) and 216a (4.30 g, 8.21 mmol) in toluene (100 mL) was added 1 M LiOMe in MeOH (7.67 mL, 7.67 mmol) via syringe. The resulting mixture was refluxed for 24 hours, cooled to room temperature, and then water (100 mL) was added. The organic phase was collected, extracted with water twice, and then dried over anhydrous sodium sulfate. After filtration and removal of the solvent in vacuo, the resulting residue was purified by flash chromatography (ethyl acetate: toluene, 1:99) to afford dimethyl ester 240 as a red solid (1.15 g, 67% yield). LC/MS (APCI): m/z 625 [M+H]$^+$.

Example 15

Preparation of ψ,ψ-Carotene-16,16'-diol (2H)

To a solution of dimethyl ester 218a (1.14 g, 1.83 mmol) in anhydrous tetrahydrofuran (100 mL) at 0° C. was added DIBAL (20% by wt. in toluene) (9.13 mL, 11.0 mmol) via syringe. The mixture was warmed to room temperature and stirred for one hour. The reaction was quenched by the sequential addition of $H_2O$ (440 μL), 15% aqueous NaOH (440 μL), and $H_2O$ (1.10 mL). The resulting mixture was stirred for 30 minutes and then dried over anhydrous $MgSO_4$. After filtration and removal of solvent in vacuo, the resulting crude diol 2H (0.39 g, 38%) was used in the next step without further purification. $^1H$ NMR (500 MHz, $CDCl_3$) δ: 6.63 (d of d, J=15.0 Hz, J=11.5 Hz, 2H, H11, H11'), 6.63 (d, J=11.0 Hz, 2H, H15, H15'), 6.48 (d of d, J=15.0 Hz, J=11.0 Hz, 2H, H7, H7'), 6.36 (d, J=15.0 Hz, 2H, H12, H12'), 6.25 (d, J=15.0 Hz, 2H, H8, H8'), 6.19 (d, J=11.5 Hz, 2H, H10, H10'), 5.95 (d, J=11.0 Hz, 2H, H6, H6'), 5.40 (t of q, J=6.50 Hz, J=1.50 Hz, 2H, H2, H2'), 4.00 (s, 4H, —$CH_2O$—), 2.19 (t, J=Hz, 4H, —$CH_2$—), 2.16 (t, J=Hz, 4H, —$CH_2$—), LC/MS (APCI): m/z 569 $[M+H]^+$.

Example 16

General Preparation of Lycophyll Derivatives

LC/MS (APCI) and LC/MS (ESI) were recorded on an Agilent 1100 LC/MSD VL, PDA detector system; column: Zorbax Eclipse XDB-C18 Rapid Resolution (4.6×75 mm, 3.5 μm); temperature: 25° C.; flow rate: 1.0 mL/min; mobile phase (% A=0.025% trifluoroacetic acid in $H_2O$, % B=0.025% trifluoroacetic acid in acetonitrile) Gradient program: 70% A/30% B (start), step gradient to 50% B over 5 min, step gradient to 98% B over 8.30 min, hold at 98% B over 25.20 min, step gradient to 30% B over 25.40 min. A catalytic amount of trifluoroacetic acid is used in the eluents to improve chromatographic resolution. The presence of trifluoroacetic acid facilitates the protonation of synthesized lycophyll dissuccinate and diphosphate salts to give the free diacid forms (as represented by the theoretical molecular ions $M^+$=768 for lycophyll dissuccinate salt and $M^+$=728 for lycophyll disphosphate salt). LRMS: +mode; ESI: electrospray chemical ionization, ion collection using quadrupole; APCI: atmospheric pressure chemical ionization, ion collection using quadrapole. Reverse-phase HPLC was performed on a Waters 996 HPLC with PDA detector, Millipore 600E System Controller system; column: Zorbax Eclipse XDB-C18 (9.4×250 mm, 5 μm); temperature: 25° C.; flow rate: 2.1 mL/min; mobile phase (% A=0.025% trifluoroacetic acid in $H_2O$, % B=0.025% trifluoroacetic acid in MeOH) Isocratic program: 15% A/85% B. $^1H$ NMR analyses were performed on a Varian spectrometer (300 MHz).

Example 17

Preparation of ψ,ψ-carotenyl 16,16'-disuccinate (222a)

To a solution of lycophyll (2H) (0.10 g, 0.176 mmol) in $CH_2Cl_2$ (2 mL) was added N,N-diisopropylethylamine (0.613 mL, 3.52 mmol) and succinic anhydride (0.1761 g, 1.76 mmol). The solution was stirred at room temperature overnight and then diluted with $CH_2Cl_2$ and quenched with cold water/1 M HCl (9/1). The aqueous layer was extracted two times with $CH_2Cl_2$ and the combined organic layer was washed three times with cold water/1 M HCl (9/1), dried over $Na_2SO_4$, and concentrated to yield disuccinate 222a (0.124 g, 92%) as a red hygroscopic solid; LC/MS (APCI): 11.59 min (65.17%), $\lambda_{max}$ 295 nm (28%), 362 nm (8%), 447 nm (72%), 472 nm (100%), 503 nm (93%), m/z 769 $[M+H]^+$ (100%), 668 $[M-C_4O_3H_4]^+$ (9%), 651(89%), 533 (30%); 12.13 min (33.69%), $\lambda_{max}$ 295 nm (26%), 362 nm (10%), 447 nm (77%), 472 nm (100%), 503 nm (91%), m/z 769 $[M+H]^+$ (28%), 651 (24%), 531 (8%), 261 (100%).

Example 18

Preparation of ψ,ψ-carotenyl 16,16'-disuccinate sodium salt (224a)

To a solution of disuccinate 222a (0.124 g, 0.161 mmol) in methanol (3 mL) at 0° C. was added dropwise sodium methoxide (25% wt in methanol; 0.074 mL, 0.322 mmol). The solution was stirred at room temperature overnight, then cooled to 0° C., and water was added. The red mixture was stirred for 5 min at 0° C., and then methanol was removed in vacuo. The red, aqueous solution was lyophilized to afford disuccinate salt 224a (0.103 g, 88%) as a red hygroscopic solid; LC/MS (APCI): 11.58 min (71.72%), $\lambda_{max}$ 295 nm (13%), 362 nm (9%), 447 nm (68%), 472 nm (100%), 503 nm (90%), m/z 769 $[M+H]^+$ (100%), 651 (42%), 533 (15%); 12.09 min (27.74%), $\lambda_{max}$ 295 nm (31%), 362 nm (19%), 447 nm (80%), 472 nm (100%), 503 nm (88%), m/z 769 $[M+H]^+$ (100%), 669 $[M-C_4O_3H_4+H]^+$ (12%), 651 (54%), 551 (8%), 533 (11%).

Example 19

Preparation of Tribenzyl phosphite (13)

To a well-stirred solution of phosphorus trichloride (1.7 mL, 19.4 mmol) in $Et_2O$ (430 mL) at 0° C. was added dropwise a solution of triethylamine (8.4 mL, 60.3 mmol) in $Et_2O$ (20 mL), followed by a solution of benzyl alcohol (8.1 mL, 77.8 mmol) in $Et_2O$ (20 mL). The mixture was stirred at 0° C. for 30 min and then at room temperature overnight. The mixture was filtered and the filtrate concentrated to give a colorless oil. Silica chromatography (hexanes/$Et_2O$/triethylamine, 5.5/1/1%) of the crude product gave 13 (5.68 g, 83%) as a clear, colorless oil that was stored under $N_2$ at −20° C.; $^1H$ NMR (300 MHz, $CDCl_3$) δ: 7.38 (15H, m), 4.90 (6H, d).

Example 20

Preparation of Dibenzyl phosphoroiodidate (14)

To a solution of tribenzyl phosphite (0.708 g, 2.01 mmol) in $CH_2Cl_2$ (5 mL) at 0° C. was added $I_2$ (0.49 g, 1.93 mmol). The mixture was stirred at 0° C. for 10 min or until the solution became clear and colorless. The solution was then stirred at room temperature for 10 min and used directly in the next step.

Example 21

Preparation of Mixture of 16,16'-Benzyl phosphoryloxy-ψ,ψ-carotenes (221a,221b,221c,221d)

To a solution of lycophyll (2H) (0.11 g, 0.193 mmol) in $CH_2Cl_2$ (5 mL) was added pyridine (0.624 mL, 7.72 mmol). The solution was stirred at 0° C. for 5 min and then freshly prepared 14 (1.93 mmol) in CH$_2$Cl$_2$ (5 mL) was added dropwise to the mixture at 0° C. The solution was stirred at 0° C. for 1 h and then diluted with CH$_2$Cl$_2$ and quenched with brine. The aqueous layer was extracted twice with CH$_2$Cl$_2$ and the combined organic layer was washed once with NaSSO$_4$, once with brine, then dried over Na$_2$SO$_4$ and concentrated. Pyridine was removed from the crude red oil by azeotropic distillation using toluene to yield a mixture of benzyl-protected diphosphoric acid lycophyll derivatives 221a,221b,221c, 221d used in the next step without further purification; LC/MS (ESI) for 221a: 10.15 min (7.73%), $\lambda_{max}$ 295 nm (21%), 362 nm (16%), 447 nm (72%), 472 nm (100%), 503 nm (87%), m/z 819 [M+H]$^+$ (18%), 800 [M–H$_2$O]$^+$ (11%), 672 (24%), 531 (10%); LC for 221b: 18.00 min (17.46%), $\lambda_{max}$ 295 nm (18%), 362 nm (13%), 447 nm (74%), 472 nm (100%), 503 nm (85%); LC for 221c: 20.08 min (20.00%), $\lambda_{max}$ 295 nm (18%), 362 nm (16%), 447 nm (74%), 472 nm (100%), 503 nm (86%); LC for 221d: 22.52 min (54.81%), $\lambda_{max}$ 295 nm (19%), 362 nm (18%), 447 nm (73%), 472 nm (100%), 503 nm (87%).

Example 22

Preparation of 16,16'-Diphosphoryloxy-ψ,ψ-carotene (221e)

To a solution of a mixture of benzyl-protected diphosphoric acid lycophyll derivatives 221a,221b,221c,221d (0.193 mmol) in CH$_2$Cl$_2$ (15 mL) at 0° C. was added dropwise N,O-bis(trimethylsilyl)acetamide (0.479 mL, 1.93 mmol) and then bromotrimethylsilane (0.203 mL, 1.54 mmol). The solution was stirred at 0° C. for 15 min, quenched with triethylamine, and stirred at 0° C. for 5 min. The red solution was then diluted with CH$_2$Cl$_2$, Et$_2$O, and MeOH (2/1/1), and then concentrated. The resulting red oil was resuspended in a minimum amount of MeOH and the cloudy solution was centrifuged to remove insoluble reaction byproducts. The red supernatant was concentrated to afford a mixture of monophosphate and diphosphate lycophyll derivatives (254/221e) (1/4) contaminated with excess reagents, and reaction and decomposition byproducts; LC/MS (ESI) for 221e: 9.10 min (39.24%), $\lambda_{max}$ 295 nm (31%), 362 nm (18%), 447 nm (74%), 472 nm (100%), 503 nm (88%), m/z 849 (25%), 827 (5%), 368(100%), 357 (11%), 317 (52%); 9.25 min (37.83%), $\lambda_{max}$ 295 nm (31%), 362 nm (18%), 447 nm (75%), 472 nm (100%), 503 nm (89%), m/z 849 (10%), 625 (8%), 581(6%), 385 (20%), 368 (100%), 357 (28%); LC/MS (ESI) for 254: 10.21 min (18.50%), $\lambda_{max}$ 295 nm (32%), 362 nm (24%), 447 nm (78%), 472 nm (100%), 503 nm (89%), m/z 648 M$^+$ (9%), 630 [M–H$_2$O]$^+$ (5%), 568 (10%), 317 (100%); the crude mixture was subjected to reverse-phase HPLC purification to give diphosphate 221e (approximately 70% pure; 0.063 g, 45%) as a red oil, contaminated with excess reagents, and reaction and decomposition byproducts; LC/MS (ESI): 9.36 min (4.43%), $\lambda_{max}$ 295 nm (30%), 362 nm (25%), 447 nm (79%), 472 nm (100%), 503 nm (82%), m/z 849 (16%), 619 (7%), 399 (23%), 368 (100%), 357 (10%), 317 (8%); 9.58 min (46.42%), $\lambda_{max}$ 295 nm (30%), 362 nm (15%), 447 nm (80%), 472 nm (100%), 503 nm (92%), m/z 849 (19%), 619 (5%), 399 (21%), 368 (100%), 357 (10%), 317 (9%); 9.67 min (49.15%), $\lambda_{max}$ 295 nm (28%), 362 nm (12%), 447 nm (77%), 472 nm (100%), 503 nm (95%), m/z 849 (15%), 619 (5%), 399 (20%), 368 (100%), 357 (8%), 317 (6%).

Example 23

Preparation of 16,16'-Diphosphoryloxy-ψ,ψ-carotene sodium salt (223a)

To a solution of lycophyll diphosphate (221e) (approximately 70% pure; 0.04 g, 0.055 mmol) in methanol (2 mL) at 0° C. was added dropwise sodium methoxide (25% wt in methanol; 0.05 mL, 0.22 mmol). The solution was stirred at room temperature overnight, then cooled to 0° C., and water was added. The red mixture was stirred for 5 min at 0° C., and then methanol was removed in vacuo. The red, aqueous solution was lyophilized to yield diphosphate salt 223a (approximately 50% pure; 0.018 g, 43%) as a red hygroscopic solid; LC/MS (ESI): 9.26 min (9.34%), $\lambda_{max}$ 295 nm (28%), 362 nm (18%), 447 nm (81%), 472 nm (100%), 503 nm (87%), m/z 897 (8%), 392 (100%), 381 (10%); 9.48 min (46.98%), $\lambda_{max}$ 295 nm (29%), 362 nm (15%), 447 nm (80%), 472 nm (100%), 503 nm (91%), m/z 911 (10%), 849 (15%), 399 (87%), 368 (100%); 9.56 min (43.68%), $\lambda_{max}$ 295 nm (28%), 362 nm (12%), 447 nm (77%), 472 nm (100%), 503 nm (90%), m/z 849 (19%), 827 (5%), 368 (100%), 357 (8%).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A chemical composition, comprising one or more carotenoid analogs or derivatives having a general structure:

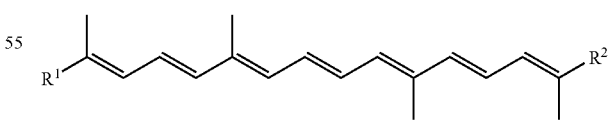

wherein each R$^1$ and R$^2$ are independently:

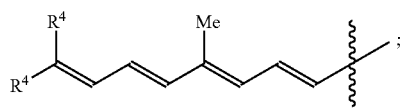

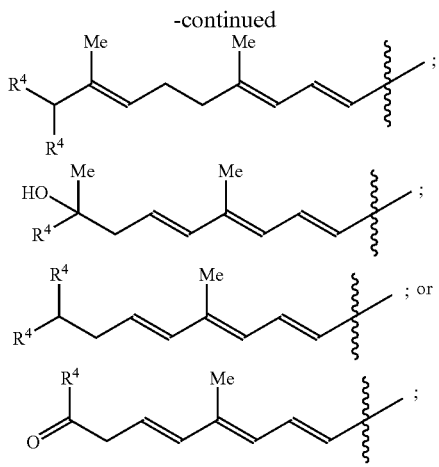

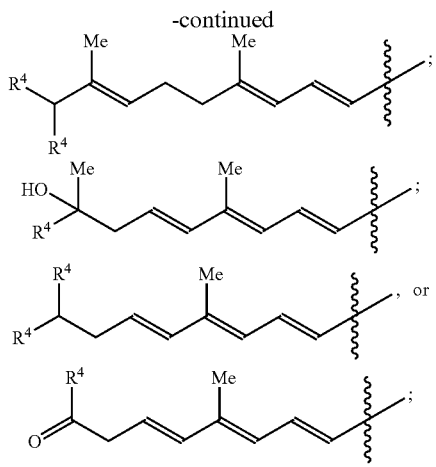

wherein:
- each $R^4$ is independently hydrogen, —OH, —$CH_2OH$, or —$OR^5$, wherein at least one $R^4$ group is —$OR^5$;
- each $R^5$ is independently: alkyl; aryl; -alkyl-N($R^7$)$_2$; -aryl-N($R^7$)$_2$; -alkyl-N$^+$($R^7$)$_3$; -aryl-N$^+$($R^7$)$_3$; -alkyl-$CO_2R^7$; -aryl-$CO_2R^7$; -alkyl-$CO_2^-$; -aryl-$CO_2^-$; —$CO_2R^8$; —P(O)(O$R^8$)$_2$; —S(O)(O$R^8$)$_2$; an amino acid; a peptide, a carbohydrate; —C(O)—(CH$_2$)$_n$—$CO_2R^9$; a nucleoside residue, or a co-antioxidant;
- $R^7$ is hydrogen, alkyl, or aryl;
- $R^8$ is hydrogen, alkyl, aryl, benzyl or a co-antioxidant;
- $R^9$ is hydrogen; alkyl; aryl; —P(O)(O$R^8$)$_2$; —S(O)(O$R^8$)$_2$; an amino acid; a peptide, a carbohydrate; a nucleoside, or a co-antioxidant;
- n is 1 to 9.

wherein:
- each $R^4$ is independently hydrogen, —OH, —$CH_2OH$, or —$OR^5$, wherein at least one $R^4$ group is —$OR^5$;
- each $R^5$ is independently: alkyl-N($R^7$)$_2$; -alkyl-N$^+$($R^7$)$_3$; -alkyl-$CO_2^-$; —P(O)(O$R^8$)$_2$; —S(O)(O$R^8$)$_2$; an amino acid; a peptide, a carbohydrate; or —C(O)—(CH$_2$)$_n$—$CO_2R^9$;
- $R^7$ is hydrogen, alkyl, or aryl;
- $R^8$ is hydrogen, alkyl, aryl, benzyl or a co-antioxidant;
- $R^9$ is hydrogen; alkyl; aryl; —P(O)(O$R^8$)$_2$; an amino acid; a peptide, a carbohydrate; a nucleoside, or a co-antioxidant;
- n is 1 to 9.

3. The chemical composition of claim 1, wherein the one or more caratenoid analogs or derivatives have a general structure:

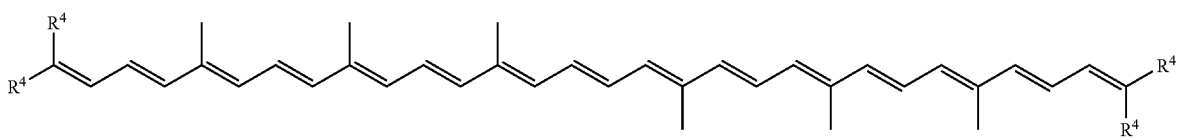

2. The chemical composition of claim 1, wherein the one or more carotenoid analogs or derivatives have a general structure:

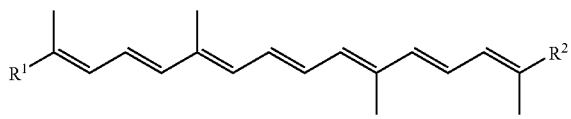

wherein each $R^1$ and $R^2$ are independently:

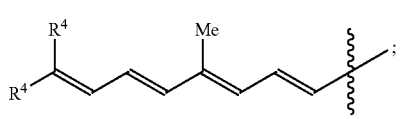

wherein:
- each $R^4$ is independently hydrogen, —OH, —$CH_2OH$, or —$OR^5$, wherein at least one $R^4$ group is —$OR^5$;
- each $R^5$ is independently: alkyl-N($R^7$)$_2$; -alkyl-N$^+$($R^7$)$_3$; -alkyl-$CO_2^-$; —P(O)(O$R^8$)$_2$; —S(O)(O$R^8$)$_2$; an amino acid; a peptide, a carbohydrate; or —C(O)—(CH$_2$)$_n$—$CO_2R^9$;
- $R^7$ is hydrogen, alkyl, or aryl;
- $R^8$ is hydrogen, alkyl, aryl, or benzyl;
- $R^9$ is hydrogen; alkyl; aryl; —P(O)(O$R^8$)$_2$; an amino acid; or a carbohydrate;
- n is 1 to 9.

4. The chemical composition of claim 1, wherein the one or more carotenoid analogs or derivatives have a general structure:

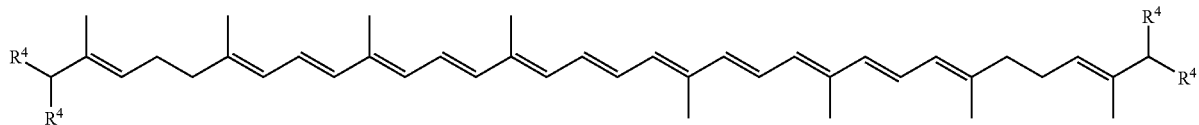

wherein:
each $R^4$ is independently hydrogen, —OH, —CH$_2$OH, or —OR$^5$, wherein at least one $R^4$ group is —OR$^5$;
each $R^5$ is independently: alkyl-N(R$^7$)$_2$; -alkyl-N$^+$(R$^7$)$_3$; -alkyl-CO$_2^-$; —P(O)(OR$^8$)$_2$; —S(O)(OR$^8$)$_2$; an amino acid; a peptide, a carbohydrate; or —C(O)—(CH$_2$)$_n$—CO$_2$R$^9$;
$R^7$ is hydrogen, alkyl, or aryl;
$R^8$ is hydrogen, alkyl, aryl, or benzyl;
$R^9$ is hydrogen; alkyl; aryl; —P(O)(OR$^8$)$_2$; an amino acid; or a carbohydrate;
n is 1 to 9.

5. The chemical composition of claim 1, wherein the one or more carotenoid analogs or derivatives have a general structure:

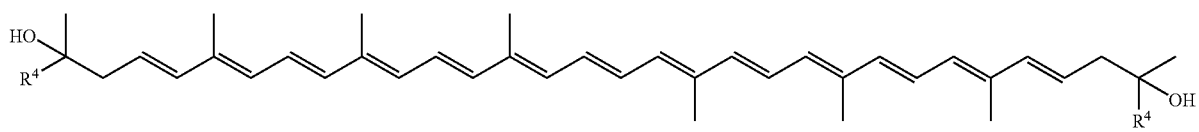

wherein:
each $R^4$ is independently hydrogen, —OH, —CH$_2$OH, or —OR$^5$, wherein at least one $R^4$ group is —OR$^5$;
each $R^5$ is independently: alkyl-N(R$^7$)$_2$; -alkyl-N$^+$(R$^7$)$_3$; -alkyl-CO$_2^-$; —P(O)(OR$^8$)$_2$; —S(O)(OR$^8$)$_2$; an amino acid; a peptide, a carbohydrate; or —C(O)—(CH$_2$)$_n$—CO$_2$R$^9$;
$R^7$ is hydrogen, alkyl, or aryl;
$R^8$ is hydrogen, alkyl, aryl, or benzyl;
$R^9$ is hydrogen; alkyl; aryl; —P(O)(OR$^8$)$_2$; an amino acid; or a carbohydrate;
n is 1 to 9.

6. The chemical composition of claim 1, wherein the one or more carotenoid analogs or derivatives have a general structure:

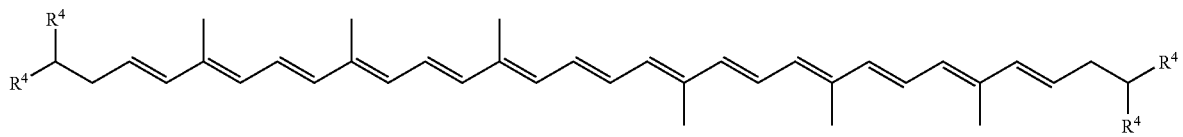

wherein:
each $R^4$ is independently hydrogen, —OH, —CH$_2$OH, or —OR$^5$, wherein at least one $R^4$ group is —OR$^5$;
each $R^5$ is independently: alkyl-N(R$^7$)$_2$; -alkyl-N$^+$(R$^7$)$_3$; -alkyl-CO$_2^-$; —P(O)(OR$^8$)$_2$; —S(O)(OR$^8$)$_2$; an amino acid; a peptide, a carbohydrate; or —C(O)—(CH$_2$)$_n$—CO$_2$R$^9$;
$R^7$ is hydrogen, alkyl, or aryl;
$R^8$ is hydrogen, alkyl, aryl, or benzyl;
$R^9$ is hydrogen; alkyl; aryl; —P(O)(OR$^8$)$_2$; an amino acid; or a carbohydrate;
n is 1 to 9.

7. The chemical composition of claim 1, wherein the one or more carotenoid analogs or derivatives have a general structure:

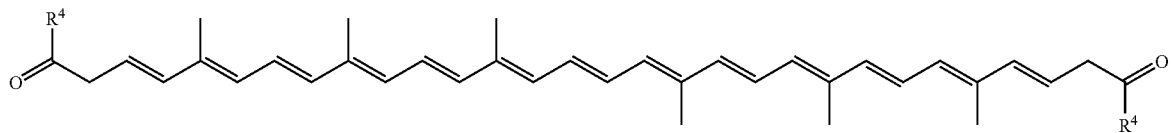

wherein:
each $R^4$ is independently hydrogen, —OH, —CH$_2$OH, or —OR$^5$, wherein at least one $R^4$ group is —OR$^5$;
each $R^5$ is independently: alkyl-N(R$^7$)$_2$; -alkyl-N$^+$(R$^7$)$_3$; -alkyl-CO$_2^-$; —P(O)(OR$^8$)$_2$; —S(O)(OR$^8$)$_2$; an amino acid; a peptide, a carbohydrate; or —C(O)—(CH$_2$)$_n$—CO$_2$R$^9$;
$R^7$ is hydrogen, alkyl, or aryl;
$R^8$ is hydrogen, alkyl, aryl, or benzyl;
$R^9$ is hydrogen; alkyl; aryl; —P(O)(OR$^8$)$_2$; an amino acid; or a carbohydrate;
n is 1 to 9.

8. The chemical composition of claim 1, wherein the one or more carotenoid analogs or derivatives have a general structure:

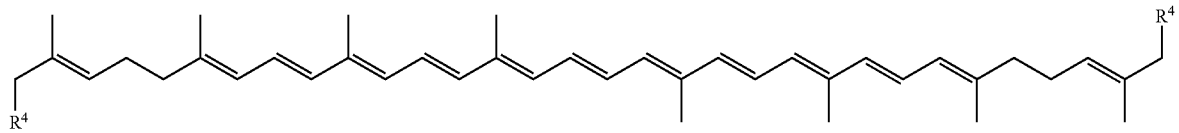

wherein:
each $R^4$ is independently —OH, or —OR$^5$, wherein at least one $R^4$ group is —OR$^5$;
each $R^5$ is independently: alkyl-N(R$^7$)$_2$ or -alkyl-N$^+$(R$^7$)$_3$; and
$R^7$ is hydrogen, alkyl, or aryl.

9. The chemical composition of claim 1, wherein the one or more carotenoid analogs or derivatives have a general structure:

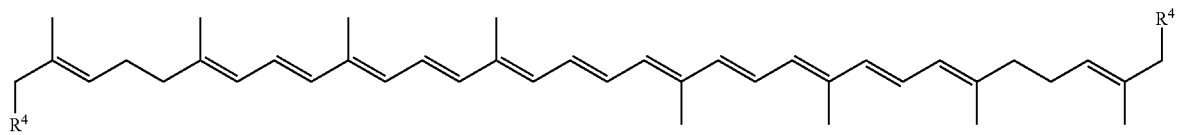

wherein:

each $R^4$ is independently —OH, or —OR$^5$, wherein at least one $R^4$ group is —OR$^5$;

each $R^5$ is independently: alkyl-CO$_2$.

10. The chemical composition of claim 1, wherein the one or more carotenoid analogs or derivatives have a general structure:

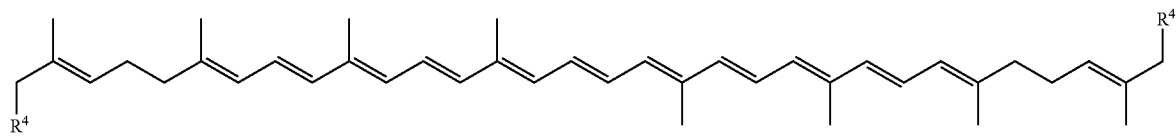

wherein:
each $R^4$ is independently —OH, or —$OR^5$, wherein at least one $R^4$ group is —$OR^5$;
each $R^5$ is independently: —$P(O)(OR^8)_2$; and
$R^8$ is hydrogen, alkyl, aryl, or benzyl.

11. The chemical composition of claim 1, wherein the one or more carotenoid analogs or derivatives have a general structure:

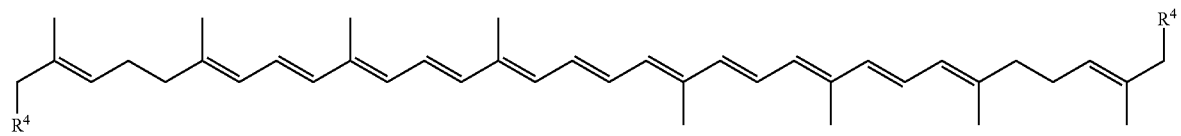

wherein:
each $R^4$ is independently —OH, or —$OR^5$, wherein at least one $R^4$ group is —$OR^5$;
each $R^5$ is independently —$S(O)(OR^8)_2$; and
$R^8$ is hydrogen, alkyl, aryl, or benzyl.

12. The chemical composition of claim 1, wherein the one or more carotenoid analogs or derivatives have a general structure:

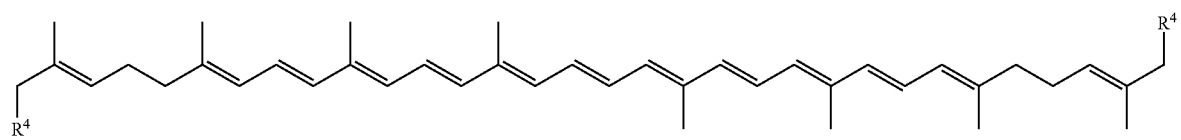

wherein:
each $R^4$ is independently —OH, or —$OR^5$, wherein at least one $R^4$ group is —$OR^5$;
each $R^5$ is independently an amino acid or a peptide.

13. The chemical composition of claim 1, wherein the one or more carotenoid analogs or derivatives have a general structure:

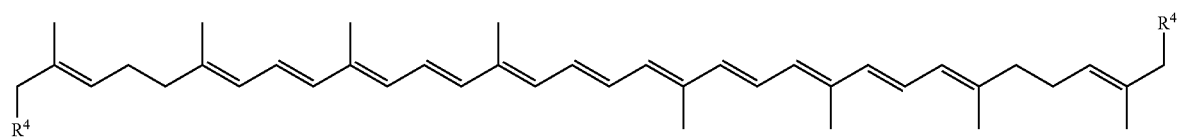

wherein:
each $R^4$ is independently —OH or —$OR^5$, wherein at least one $R^4$ group is —$OR^5$;
each $R^5$ is independently:
—$CH_2$—$(CHOH)_n$—$CO_2H$;
—$CH_2$—$(CHOH)_n$—CHO;
—$CH_2$—$(CHOH)_n$—$CH_2OH$;
—$CH_2$—$(CHOH)_n$—C(O)—$CH_2OH$;

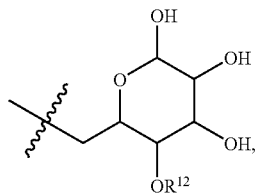

where $R^{12}$ is hydrogen or

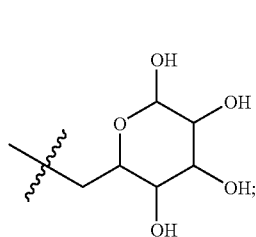

or

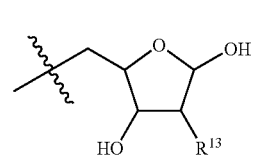

where $R^{13}$ is hydrogen or —OH.

14. The chemical composition of claim 1, wherein the one or more carotenoid analogs or derivatives have a general structure:

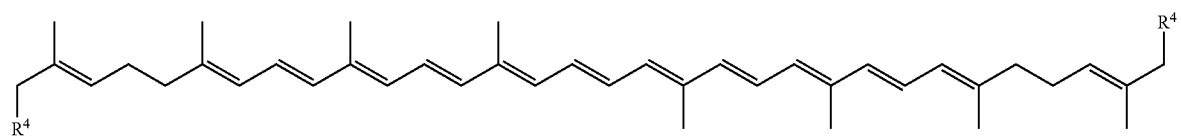

wherein:
each $R^4$ is independently —OH or —$OR^5$, wherein at least one $R^4$ group is —$OR^5$; each $R^5$ is independently —C(O)—$(CH_2)_n$—$CO_2R^9$;
$R^9$ is hydrogen; alkyl; aryl; —P(O)($OR^8$)$_2$; an amino acid; or a carbohydrate; and
n is 1 to 9.